(12) United States Patent
Bhowmik

(10) Patent No.: US 11,298,555 B2
(45) Date of Patent: Apr. 12, 2022

(54) FEEDTHROUGH CONNECTORS IN GLASS

(71) Applicant: BIOTRONIK SE & CO. KG, Berlin (DE)

(72) Inventor: Siddhartha Bhowmik, Lake Oswego, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 43 days.

(21) Appl. No.: 16/514,012

(22) Filed: Jul. 17, 2019

(65) Prior Publication Data

US 2020/0023187 A1 Jan. 23, 2020

Related U.S. Application Data

(60) Provisional application No. 62/698,997, filed on Jul. 17, 2018.

(51) Int. Cl.
*A61N 1/375* (2006.01)
*H01R 13/52* (2006.01)

(52) U.S. Cl.
CPC ....... *A61N 1/3754* (2013.01); *H01R 13/5224* (2013.01); *H01R 2201/12* (2013.01)

(58) Field of Classification Search
CPC .......................... A61N 1/3754; H01R 13/5224
USPC ................ 607/36, 37; 174/262, 264; 29/851
See application file for complete search history.

(56) References Cited

U.S. PATENT DOCUMENTS

| | | | | |
|---|---|---|---|---|
| 5,818,002 A * | 10/1998 | Kurtz | ................... | H01H 35/346 200/83 Y |
| 8,528,201 B2 * | 9/2013 | Troetzschel | ......... | A61N 1/3754 29/851 |
| 8,844,103 B2 * | 9/2014 | Iyer | ........................ | H05K 13/00 29/25.42 |
| 9,032,614 B2 * | 5/2015 | Specht | ............... | H01R 13/5224 29/851 |
| 9,403,023 B2 * | 8/2016 | Markham | ............ | A61N 1/3754 |
| 9,552,899 B2 * | 1/2017 | Specht | ................... | H01B 1/023 |
| 2007/0060970 A1 | 3/2007 | Burdon et al. | | |
| 2011/0190885 A1 | 8/2011 | Troetzschel et al. | | |
| 2014/0360748 A1 | 12/2014 | Iyer et al. | | |
| 2020/0023187 A1 * | 1/2020 | Bhowmik | ................ | H01G 4/35 |

* cited by examiner

*Primary Examiner* — Neil Abrams
(74) *Attorney, Agent, or Firm* — Laurence A. Greenberg; Werner H. Stemer; Ralph E. Locher

(57) ABSTRACT

A feedthrough connector contains an electrically insulating body formed from glass. The body has a front side and a back side facing away from the front side. The body further has a circumferential lateral side extending from the front side to the back side of the body. The body has a plurality of through-openings, wherein each through-opening extends from the front side to the back side of the body. A plurality of electrical conductors is provided and, each conductor is arranged in one of the through-openings to hermetically seal the respective through-opening. The respective conductor contains a metallic material. A first end of the conductor is arranged at the front side and is connected to a first contact pad arranged on the front side, and an opposing second end is arranged at the back side and is connected to a second contact pad arranged on the back side. A method for producing the feedthrough connector includes to provide blind holes in the body with metallic material filled into the blind holes to define conductors.

11 Claims, 17 Drawing Sheets

FEEDTHROUGH CONNECTORS IN GLASS

CROSS-REFERENCE TO RELATED APPLICATION

This application claims the priority, under 35 U.S.C. § 119(e), of provisional application No. 62/698,997 filed Jul. 17, 2018; the prior application is herewith incorporated by reference in its entirety.

BACKGROUND OF THE INVENTION

Field of the Invention

The present invention relates to a feedthrough connector, particularly for an implantable medical device, an implantable medical device, as well as to a method for producing a feedthrough connector.

A hermetic feedthrough connector usually is an expensive component that requires high reliability. Such feedthroughs and interconnects are critical parts of implantable medical devices that provide an interface between the electronics inside a housing of the device and the outside system in the human body. Bio-compatibility and reliability are critical. Additionally with miniaturization these components it is desirable to shrink such components and to have them compatible with integration to next level assembly.

Therefore, reliable low cost solutions are desired to produce feedthroughs which can meet these goals. Particularly, traditional pin type feedthroughs use Nb or Pt/Ir pins that are brazed (usually with Au) into a ceramic which in turn is Au brazed to a flange (usually Ti) that interfaces with the device's housing. Furthermore, feedthroughs can also be made with a HTCC (High Temperature Cofired Ceramic) technology that use Pt pastes applied to ceramic substrates and sequentially fired in a fashion similar to LTCC substrate manufacturing. However, standard pin based feedthroughs component miniaturization is limited. Furthermore, costs are high on standard pin feedthroughs due to labor content, while HTCC feedthroughs require many layers to achieve needed hermiticity (>10) of the feedthrough.

Based on the above, it is an object of the present invention to provide a reliable feedthrough connector that can be produced in a relatively easy fashion allowing miniaturization, simplicity and volume fabrication.

SUMMARY OF THE INVENTION

This problem is solved by a feedthrough connector, a method for producing such a feedthrough connector, and an implantable medical device comprising a feedthrough connector according to the present invention.

With the foregoing and other objects in view there is provided, in accordance with the invention, a feedthrough connector, comprising:

an electrically insulating body formed out of a glass, the body comprising a front side and a back side facing away from the front side, wherein the body further comprises a circumferential lateral side extending from the front side to the back side of the body, and wherein the body comprises a plurality of through-openings, wherein each through-opening extends from the front side to the back side of the body, a plurality of electrical conductors (also denoted as TGVs for through glass vias), each conductor arranged in one of the through-openings to hermetically seal the respective through-opening, wherein the respective conductor comprises or is formed out of a metallic material, wherein the respective conductor further comprises a first end arranged at the front side and connected to a first contact pad arranged on the front side, and an opposing second end arranged at the back side and connected to a second contact pad arranged on the back side of the body, and a circumferential flange comprising or formed out of a metallic material, wherein the flange is connected to the lateral side of the body such that the flange surrounds the body and contacts the lateral side of the body.

Advantageously, the design according to the present invention allows using standard manufacturing technologies using a glass-based substrate (e.g. wafer) to create reliable interconnecting feedthroughs.

Particularly, according to an embodiment of the present invention, the flange covers a majority of the lateral side of the body. Particularly, the flange covers the lateral side of the body completely.

Further, according to an embodiment of the present invention, the flange contacts the lateral side of the body in a hermetically sealed fashion.

Furthermore, according to an embodiment of the present invention, the respective through-opening can comprise a first section starting at the front side of the body and connected to a second section of the respective through-opening extending to the back side of the body. The first and the second section of the respective through opening are arranged offset with respect to one another so that the respective through-opening and the conductor arranged therein comprise a narrowing. The flange particularly covers a circumferential section of the lateral side, which section comprises a height corresponding to a length (in a direction perpendicular to the front side of the body) of the first section of the respective through opening.

Furthermore, according to an embodiment of the present invention, the body and/or the body together with the flange thereon forms a cuboid, particularly a rectangular cuboid. Particularly, the respective edge of the cuboid (e.g. rectangular cuboid) can also be rounded.

Particularly, the flange is adapted such that it is weldable or brazeable to another component such as a housing of an implantable medical device.

Particularly, according to an embodiment of the present invention, the feedthrough connector may comprise six through openings and corresponding conductors, wherein the conductors can be arranged in two parallel rows, each row comprising three conductors.

Furthermore, according to an embodiment of the present invention, the glass is one of or comprises one of: $SiO_2$, a borosilicate (e.g. the glass can be a borosilicate glass), a glass composition tailored to match the coefficient of thermal expansion (CTE) of the metallic material of the conductor and/or of the further metallic material of the flange.

Further, according to an embodiment of the present invention, the metallic material comprised by or forming the respective conductor, is one of: Ti, Ta, Ni, W, an alloy comprising Ti and Al, an alloy comprising Ti and Ni, an alloy comprising Ti and W.

Further, according to an embodiment of the present invention, the further metallic material comprised by or forming the flange is one of: Ti, Ta, Ni, W, an alloy comprising Ti and Al, an alloy comprising Ti and Ni, an alloy comprising Ti and W.

Particularly, in an embodiment, the further metallic material of the flange is identical to the metallic material of the conductor, e.g. so as to minimize deposition steps (see also below).

Furthermore, according to an embodiment of the present invention, the respective first contact pad arranged on the front side of the electrically insulating body comprises or is formed out of a further metallic material. The further metallic material of the respective first contact pad is particularly one of: Au, Pt, Nb, Rh, Ti, an alloy comprising at least one of Au, Pt, Nb, Rh, Ti.

Further, according to an embodiment of the present invention, the respective second contact pad arranged on the back side of the electrically insulating body comprises or is formed out of a further metallic material. The further metallic material of the respective second contact pad is particularly one of: Sn/Ni; Ag; Au; an alloy comprising Sn, Ag, and Cu; an alloy comprising Sn and Pb. Sn/Ni is a metal bilayer where Ni is deposited first followed by Sn.

Further, according to an embodiment of the present invention, the first contact pads on the front side of the body of the feedthrough connector are configured to be arranged outside a housing of an implantable medical implant device. Furthermore, in an embodiment, the second contact pads on the back side of the body of the feedthrough connector are configured to be connected to an electrical circuit enclosed by the housing. The feedthrough connector thus provides electrical connection between the electrical circuit and a component (such as a header) arranged outside the housing.

Further, according to an embodiment of the present invention, the electrically insulating body of the feedthrough connector comprises a height corresponding to a distance between the front side and the back side of the body (e.g. in a direction along which the respective conductor extends between the front side and the back side of the body or in a direction perpendicular to the front side and/or the back side of the body) that is in the range from 0.5 mm to 1.5 mm.

Further, according to an embodiment of the present invention, a minimal distance of the respective first contact pad to an edge of the front side of the body of the feedthrough connector is in the range from 0.25 mm to 1.0 mm. Further, in an embodiment, a minimal distance of the respective second contact pad to an edge of the back side of the body is in the range from 0.25 mm to 1.0 mm.

Further, according to an embodiment of the present invention, the flange comprises a thickness in a direction perpendicular to the lateral side of the body of the feedthrough connector that is in the range from 0.2 mm to 3.0 mm.

Further, according to an embodiment of the present invention, the flange comprises a height in a direction along which the respective conductor extends between the front side and the back side of the body (or in a direction perpendicular to the front side and/or the back side of the body of the feedthrough connector) that is in the range from 0.5 mm to 1.5 mm.

Further, according to an embodiment of the present invention, each first or second contact pad can comprise a quadrangular or circular contact surface.

Further, according to an embodiment of the present invention, the respective first contact pad can comprise a thickness in a direction perpendicular to the front side of the body that is in the range from 0.05 mm to 0.5 mm.

Further, according to an embodiment of the present invention, the respective second contact pad can comprise a thickness in a direction perpendicular to the front side of the body of the feedthrough connector that is in the range from 0.05 mm to 0.5 mm.

Further, according to an embodiment of the present invention, the respective first contact pad can comprise a width in a direction parallel to the front side of the body of the feedthrough connector that is in the range from 0.1 mm to 1 mm.

Further, according to an embodiment of the present invention, the respective second contact pad can comprise a width in a direction parallel to the back side of the body of the feedthrough connector that is in the range from 0.1 mm to 1 mm.

Further, according to an embodiment of the present invention, the respective conductor can comprise a length (e.g. in the direction of the height of the body of the feedthrough connector or in a direction perpendicular to the front side and/or to the back side of the body of the feedthrough connector) that is in the range from 0.5 mm to 1.5 mm (corresponding e.g. to the height of the body and/or of the flange).

Further, according to an embodiment of the present invention, the respective conductor can comprise a diameter (particularly in a direction parallel to the front side and/or to the back side of the body of the feedthrough connector, or in a direction perpendicular to the length of the respective conductor or perpendicular to the height of the body and/or of the flange) that is in the range from 0.01 mm to 0.5 mm.

A further aspect of the present invention relates to a method for producing a feedthrough connector according to the present invention.

Particularly, the method for producing the feedthrough connector comprises the steps of:

providing a glass wafer (e.g. a circular wafer having diameter in the range from e.g. 100 mm to 300 mm) comprising a wafer portion or a plurality of wafer portions connected to each other, each wafer portion comprising a front side and a back side facing away from the respective front side, forming a plurality of blind holes and a circumferential recess in the front side of the respective wafer portion such that the recess surrounds the blind holes, and filling a metallic material in the blind holes of the respective wafer portion to form conductors, wherein each conductor comprises a first end at the front side of the respective wafer portion and a second end at a bottom of the respective blind hole, and filling a further metallic material in the recess of the respective wafer portion to form a flange of the respective wafer portion.

According to an embodiment of the method according to the present invention, the metallic material of the conductors and the further metallic material of the flanges can be identical. The metallic materials already stated above may be used.

Further, according to an embodiment of the method according to the present invention, the respective blind hole and/or the respective recess can be formed in the front side of the respective wafer portion by a patterning the front side of the respective wafer portion with a photoresist (PR) followed by a dry etching process such as e.g. RIE (reactive ion etching), or e.g. inductive coupled plasma (ICP) etch, or e.g. ion milling.

Alternatively, a suitable Laser can be used to form the blind holes (holes do not break through to the back side of the body) and/or the recess into the front side of the respective wafer portion.

Further, according to an embodiment of the method according to the present invention, the diameter of the respective through-opening or conductor perpendicular to the front side or back side of the respective wafer portion can be in the range from 0.01 mm to 0.5 mm, and the respective blind hole can have a depth in the range from 50% to 95% of the glass wafer height in a direction perpendicular to the respective front side or back side of the wafer portion (see also above).

As already mentioned above, the respective recess/flange can have a thickness in the range from 0.2 mm to 3.0 mm and a depth (height) of 50% to 95% of the height of the glass wafer/respective wafer portion (see also above).

Further, according to an embodiment of the method according to the present invention, a coating is applied to an inner side of the respective blind hole of the respective wafer portion before the metallic material is filled in the blind holes of the respective wafer portion, and/or wherein a coating is applied to an inner side of the recess of the respective wafer portion before the further metallic material is filled in the recess of the respective wafer portion.

Further, according to an embodiment of the method according to the present invention, the coating of the inner sides of the blind holes or of the recesses can be a metallization. Particularly, the respective coating (e.g. metallization) acts as an adhesion layer. The coating can comprise one of Ti, Ta, an alloy comprising Ti and W, Ni (e.g. in form of a Ni seed layer). The respective coating can be applied through one of: physical vapor deposition (PVD), sputtering, evaporation.

Further, according to an embodiment of the method according to the present invention, a thickness of the respective coating can be in the range from 0.1 µm to 1 µm.

Further, according to an embodiment of the method according to the present invention, the blind holes and/or the recess of the respective wafer portion can be filled (e.g. after applying the coating) with the respective metallic material by a CVD process (depositing of e.g. one of W, Ni, Ti), or by plating (e.g. Ni).

For both of these filling methods (plating or CVD), a chemical mechanical polish (CMP) can be applied afterward to the front side of the respective wafer portion to planarize the respective front side.

Further, according to an embodiment of the method according to the present invention, the method further comprises the step of masking the front side of the respective wafer portion by a mask such that the first ends of the conductors at the front side of the respective wafer portion are left free by the mask. A further metallic material is deposited on the non-covered first ends of the conductors to form first contact pads thereon. The mask is removed from the front side of the respective wafer portion after forming of the first contact pads.

Further, according to an embodiment of the method according to the present invention, the mask may be formed out of a thin metal or polymer foil with precise holes that are aligned on top of the front side of the respective wafer portion with the respective first ends of the conductors (i.e. with the positions of the blind holes on the front side of the respective waver portion).

Further, according to an embodiment of the method according to the present invention, the further metallic material for the first contact pads can comprise or can be formed by the materials stated above with respect to the first contact pads. Particularly, a metal such as e.g. one of Au, Pt, Nb, Ti can be evaporated or sputtered onto the first ends of the conductors. The thickness (in a direction perpendicular to the front side of the respective wafer portion) of the respective first contact pad formed in this way can be in the range from 0.05 mm to 0.5 mm (see also above).

Further, according to an embodiment of the method according to the present invention, the method further comprises the step of removing a layer on the back side of the respective wafer portion so as to expose the second ends of the conductors of the respective wafer portion.

Further, according to an alternative embodiment of the method according to the present invention, the method further comprises the step of forming a plurality of holes in the back side of the respective wafer portion, wherein each of the holes is arranged offset (in a direction parallel to the back side of the body) with respect to an associated blind hole formed in the front side of the respective wafer portion, such that the respective hole exposes a portion of the conductor in the associated blind hole, and filling the metallic material into the holes in the back side of the respective wafer portion to form a narrowing of the respective conductor and to prolong the respective conductor such that it extends with its second end towards the back side of the respective wafer portion. Also here, a coating can be applied to an inner side of the respective hole formed in the back side of the respective wafer portion (using e.g. one of the materials stated above with respect to the coating of the blind holes) before the metallic material is filled into the holes to extend the conductors to the back side of the respective wafer portion. The narrowing of the conductor leads to a feedthrough that is particularly impermeable to liquids.

Further, according to an embodiment of the method according to the present invention, the back side of the respective wafer portion is masked by a mask such that the second end of the respective conductor at the back side of the respective wafer portion is left free. A further metallic material is deposited on the non-covered second end of the respective conductor to form a second contact pad connected to the respective conductor, and the mask is removed from the back side of the respective wafer portion after forming of the second contact pads.

Further, according to an embodiment of the method according to the present invention, the further metallic material for the second contact pads can comprise or can be formed by the materials stated above with respect to the second contact pads.

Particularly, the further metallic material can comprise or can be one of the following (e.g. solderable) metals: Sn/Ni, Cu/Ni, Sn/Pb, Pt, Rh, Nb, an alloy comprising Sn, Ag, and Cu.

Further, according to an embodiment of the method according to the present invention, the method further comprises the steps of mounting the glass wafer on a carrier, wherein particularly the front side of the respective wafer portion is arranged on the carrier, i.e. faces towards the carrier.

Further, according to an embodiment of the method according to the present invention, the method further comprises the step of removing a region of the wafer portion that surrounds the flange of the respective wafer portion so that a circumferential lateral side of the flange of the respective wafer portion is exposed and the respective wafer portion forms an electrically insulating body of a feed through connector resting on the carrier. When several wafer portions are attached to each other this step also leads to separating the wafer portions from one another.

The method according to the invention therefore allows producing feedthroughs directly with an integrated flange. In previous methods, a flange had to be added separately after the production of the feedthrough element itself by for example brazing a metal flange to the glass insulator. The present method is therefore more efficient and less expensive than previous methods.

Further, according to an embodiment of the method according to the present invention, before the step of removing a region of the wafer portion that surrounds the flange of the respective wafer portion (and thereby separating the wafer portions from one another when several wafer portions are present), a mask is arranged on the back side of the/each wafer portion, which mask extends on the back side of the respective wafer portion up to an outer edge of the flange of the respective waver portion so that the region of the respective wafer portion is not covered but left free for removal.

Particularly, the mask (protective metal) can be formed by Ni or Al metal layers highly selective to dry etch chemistry for glass wafer. Alternatively, conventional lithography can be used to deposit a mask such as SU8 on the back side of the respective wafer portion.

Further, according to an embodiment of the method according to the present invention, the region of the respective wafer portion is then removed by an etching process.

Further, according to an embodiment of the method according to the present invention, a RIE dry etching process can be used to remove the region of the respective wafer portion.

Alternatively, the region of the respective wafer portion can be removed by means of a laser to separate the wafer portion that surrounds the flange/the wafer portions/feedthrough connectors from one another.

Particularly, such a laser-based separation can be followed by a wet or dry chemical process to remove residual glass and expose the flange of the respective wafer portion/feedthrough connector.

An etching gas used in an etching process described above can be a fluorine-based plasma, particularly a $C_4F_8$ plasma, or $CF_4$ plasma, or $SF_6$.

Furthermore, the respective mask can be removed by a wet or dry ash process (depending on material used for the respective mask).

Furthermore, yet another aspect of the present invention relates to an implantable medical device comprising a feedthrough connector according to the present invention.

According to an embodiment, the medical device comprises a housing that is welded to the flange of the feedthrough connector.

Furthermore, according to an embodiment of the medical device, the first contact pads of the feedthrough connector are arranged outside the housing.

Further, according to an embodiment of the medical device, the second contact pads of the feedthrough connector are arranged in an internal space enclosed by the housing. Particularly, the second contact pads can be connected to an electrical circuit of the medical device arranged in the internal space. Particularly, the electrical circuit can be arranged on a substrate arranged in the internal space. The substrate can be a printed circuit board.

Particularly, the present invention using glass-based feedthroughs advantageously allows highly parallel processing of many feedthroughs by using glass wafers or panels with semiconductor-based processing equipment and process recipes. For example, a 200 mm glass wafer allows processing of upwards of 1000 feedthroughs in parallel. Thus, production costs can be significantly reduced. The technology further allows reduced pad to pad or contact to contact pitches as might be needed for Neurological implants that require a high I/O count therapy.

Other features which are considered as characteristic for the invention are set forth in the appended claims.

Although the invention is illustrated and described herein as embodied in feedthrough connectors in glass, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
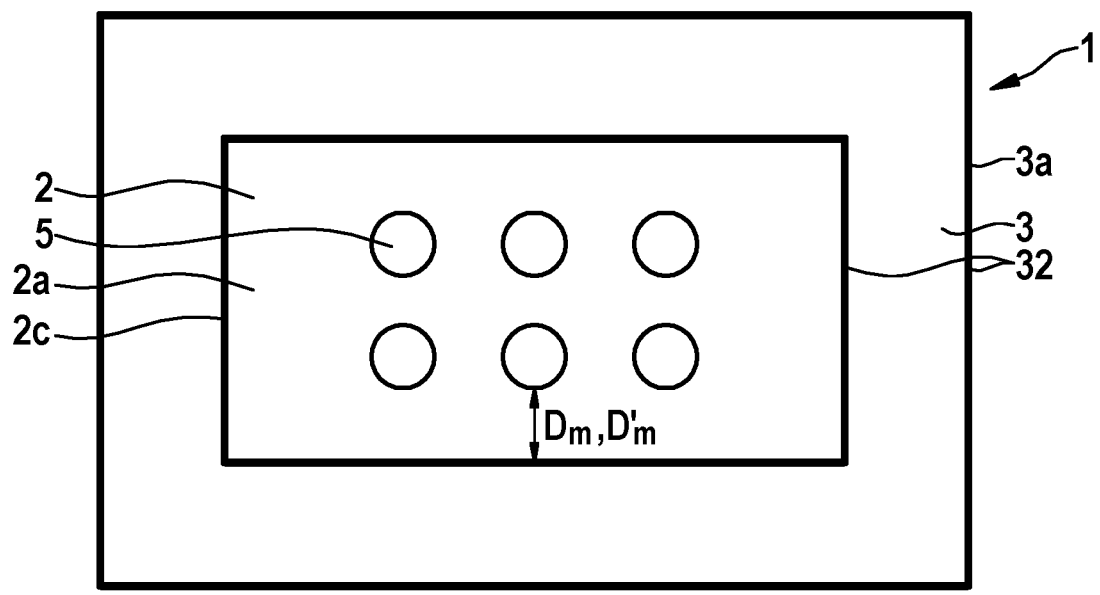
FIG. 1 is a schematical plan view onto a front side of a feedthrough connector according to the present invention.
Figure 2:
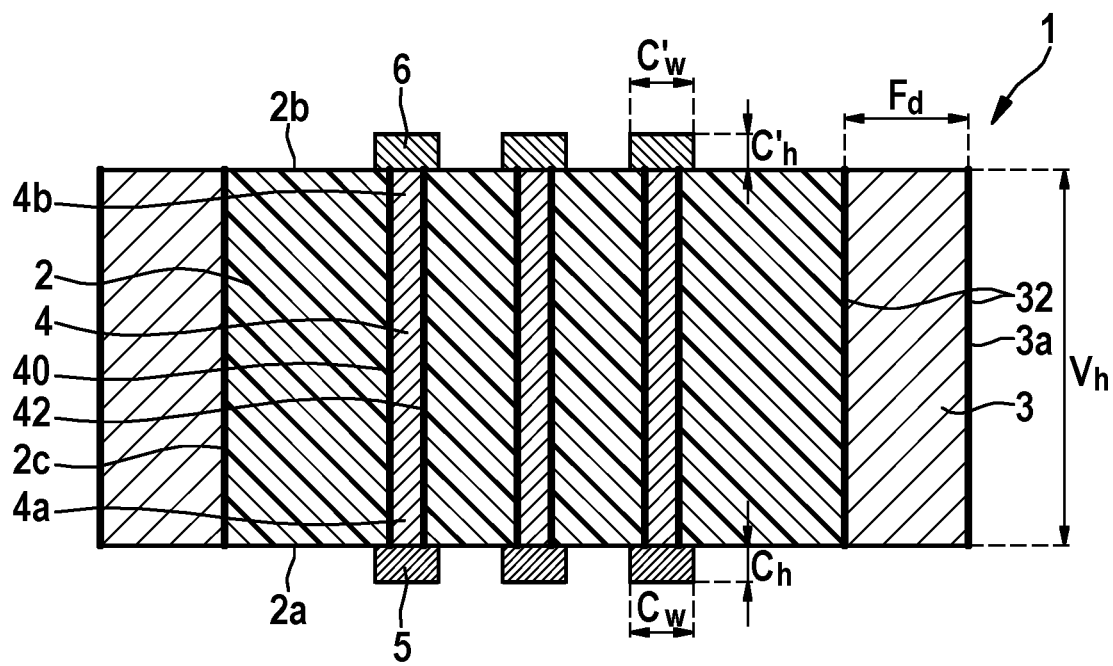
FIG. 2 is a schematical cross sectional view of the feedthrough connector shown in FIG. 1.

Referring now to the figures of the drawings in detail and first, particularly to FIGS. 1 and 2 thereof, there is shown an embodiment of a feedthrough connector 1 according to the present invention. The feedthrough connector 1 comprises an electrically insulating body 2 formed out of a glass, wherein the body 2 further comprises a front side 2a and a back side 2b that faces away from the front side 2a, wherein the body 2 further comprises a circumferential lateral side 2c extending from the front side 2a to the back side 2b of the body 2. The body/insulator 2 further comprises a plurality of through-openings 40, wherein each through-opening 40 extends from the front side 2a to the back side 2b of the body 2, and a corresponding plurality of electrical conductors 4, wherein each conductor 4 is arranged in one of the through-openings 40 such that the respective through-opening 40 is hermetically sealed. The respective conductor 4 comprises a metallic material, a first end 4a arranged at the front side 2a and connected to a first contact pad 5 arranged on the front side 2a, and an opposing second end 4b arranged at the back side 2b and connected to a second contact pad arranged 6 arranged on the back side 2b. Furthermore, the feedthrough connector 1 comprises a circumferential flange 3 comprising a further metallic material, wherein the flange 3 is connected to the lateral side 2c of the body 2 such that the flange 3 surrounds the body 2 and contacts the lateral side 2c of the body 2.

As shown in FIG. 2, the flange 3 can cover the entire lateral side 2c of the electrically insulating body 2 of the connector 1.

According to an embodiment of the feedthrough connector 1 shown in FIGS. 26 and 27 (see also below), the respective through-opening 40 of the connector 1 can comprise a first section 40a starting at the front side 2a of the body 2 and connected to a second section 40b extending to the back side 2b of the body 2 (cf. FIG. 26). The first and the second sections 40a, 40b of the respective through-opening 40 are arranged offset with respect to one another so that the respective through-opening 40 comprises a narrowing 401, wherein the flange 3 particularly covers a circumferential section 2cc of the lateral side 2c, which section 2cc comprises a height $H_{cc}$ corresponding to a length $V_{40a}$ (in a direction perpendicular to the front side 2a and/or back side 2b) of the first section 40a of the respective through-opening 40 (cf. FIG. 26). Alternatively however, the flange could extend along the entire length height $V_h$ of the wafer.

For forming the conductors 4, the first and second contact pads 5, 6 as well as the flanges the metallic materials described herein can be used.

Further, particularly, the first contact pads 5 on the front side 2a of the body 2 are configured to be arranged outside a housing 12 of an implantable medical implant device 11, and/or the second contact pads 6 on the back side 2b of the body 2 are configured to be connected to an electrical circuit 13 enclosed by the housing 12, which circuit can be arranged on a substrate 14 such as a printed circuit board. The feedthrough connector 1 thus provides electrical connection between the electrical circuit 13 and a component (such as a header) arranged outside the housing 12.

As indicated in FIG. 2, according to an embodiment of the present invention, the body 2 can comprise a height $V_h$ corresponding to a distance between the front side 2a and the back side 2b of the body 2 that is in the range from 0.3 mm to 1.5 mm.

Furthermore, as indicated in FIG. 1, according to an embodiment of the present invention, a minimal distance $D_m$ of the respective first contact pad 5 to an edge of the front side 2a of the body 2 is in the range from 0.25 mm to 1.0 mm. Further, according to an embodiment, a minimal distance $D'_m$ of the respective second contact pad 6 to an edge of the back side 2b of the body 2 is in the range from 0.25 mm to 1.0 mm.

Further, as indicated in FIG. 2, in an embodiment, the flange 3 can comprise a thickness $F_d$ in a direction normal to the lateral side 2c of the flange 3 that is in the range from 0.2 mm to 3.0 mm.

Figure 5:
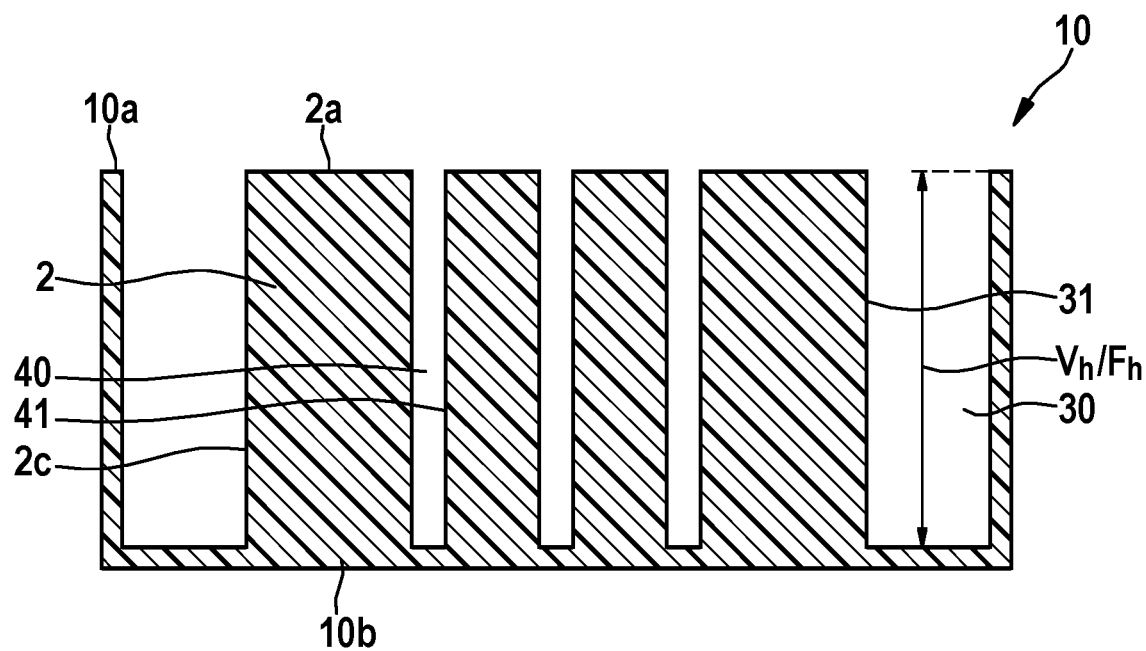
FIG. 5 is a schematical cross sectional view of the wafer portion shown in FIG. 4.

Further, as indicated in FIG. 5, according to an embodiment, the flange 3 comprises a height $F_h$ in a direction along which the respective conductor 4 extends between the front side 2a and the back side 2b of the body 2 (or in a direction perpendicular to the front side 2a and/or back side 2b of the body 2) that is in the range from 0.3 mm to 1.5 mm.

Furthermore, in an embodiment, the respective first contact pad 5 can comprise a thickness $C_h$ in a direction normal to the front side 2a of the body 2 that is in the range from 0.05 mm to 0.5 mm (cf. FIG. 2). Further, in an embodiment, the respective second contact pad 6 can comprise a thickness $C'_h$ in a direction normal to the back side 2b of the body 2 that is in the range from 0.05 mm to 0.5 mm (cf. FIG. 2).

Furthermore, in an embodiment, the respective first contact pad 5 can comprise a width $C_w$ in a direction parallel to the front side 2a of the body 2 that is in the range from 0.1 mm to 1 mm (cf. FIG. 2). Likewise, in an embodiment, the respective second contact pad 6 can comprise a width $C'_w$ in a direction parallel to the back side 2b of the body 2 that is in the range from 0.1 mm to 1 mm (cf. FIG. 2).

Furthermore, according to an embodiment, the respective conductor 4 can comprise a length (e.g. in the direction of the height of the body 2) $V_h$ as indicated in FIG. 2 that is in the range from 0.5 mm to 1.5 mm (corresponding e.g. to the height $V_h$ of the body 2 and of the flange 3).

Figure 4:
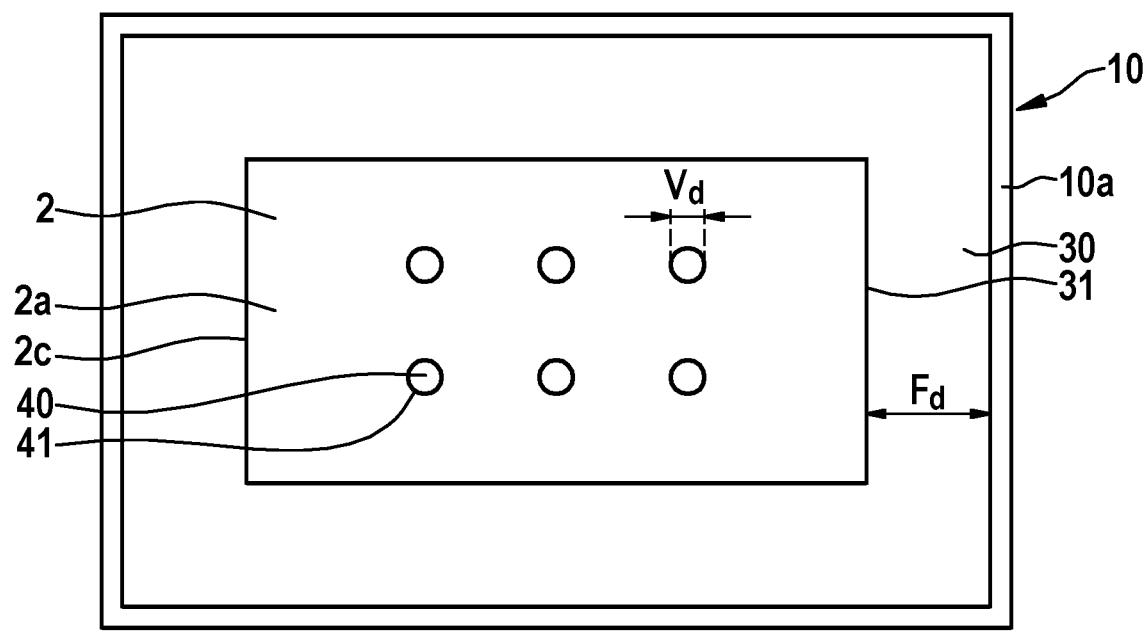
FIG. 4 is a schematical plan view onto a wafer portion of the glass wafer shown in FIG. 3 after forming blind holes and a circumferential recess into a front side of the wafer portion.

Furthermore, in an embodiment, as indicated in FIG. 4, the respective conductor 4 can comprise a diameter $V_d$, particularly perpendicular to the length $V_h$ of the respective conductor 4 or perpendicular to the height $V_h$ of the body 2 and/or flange 3 that is in the range from 0.01 mm to 0.5 mm.

Particularly, the individual dimensions of the feedthrough connector 1 stated above can be combined in any reasonable manner.

Particularly, the feedthrough connector 1 shown in FIGS. 1 and 2 can be produced using a method according to the present invention which shall be described in more detail below.

Figure 3:
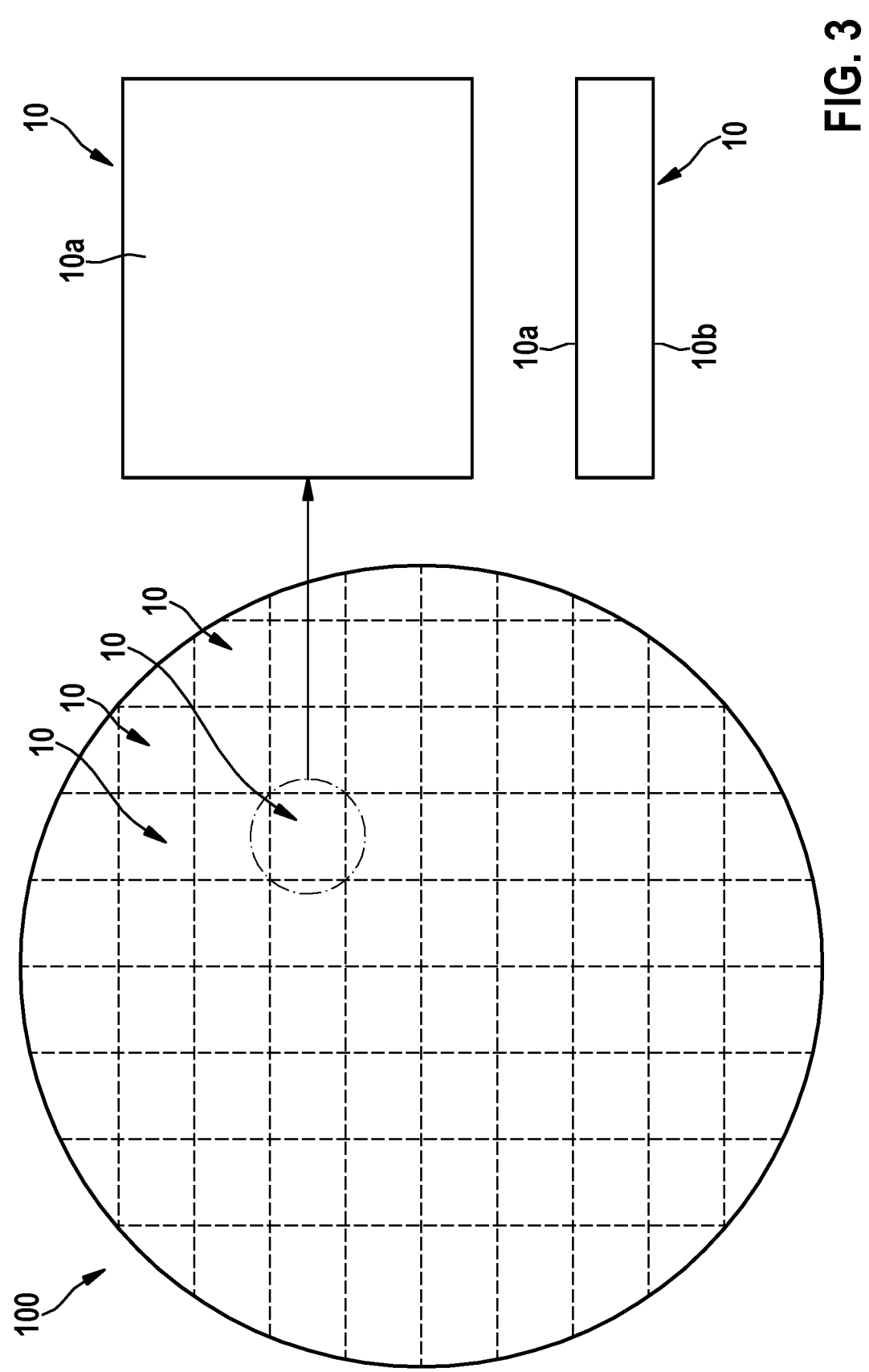
FIG. 3 is an illustration of a glass wafer that can be used to produce multiple feedthrough connectors of the kind shown in FIGS. 1 and 2 in a parallel fashion.

According to the method, a glass wafer 100 (e.g. circular wafer having diameter in the range from e.g. 100 mm to 300 mm) is provided as shown in FIG. 3, which comprises a plurality of adjacent wafer portions 10, wherein each wafer portion 10 comprises a front side 10a and a back side 10b facing away from the respective front side.

The respective wafer portion 10 will form the body 2 of the respective final feedthrough connector 1 and will be provided with conductors 4, contact pads 5, 6 and a flange during the process.

As further indicated in FIGS. 4 and 5 a plurality of blind holes 40 are formed in the front side 10a of the respective wafer portion 10 and a circumferential recess 30 such that the recess 30 surrounds the blind holes 40. Particularly, the blind holes 40 and/or the recess 30 of the respective wafer portion 10 can have e.g. a depth $V_h$ in the range from 50% to 95% of the glass wafer's 100 height in a direction perpendicular to the respective front side 2*a* or back side 2*b* (see also above).

Figure 6:
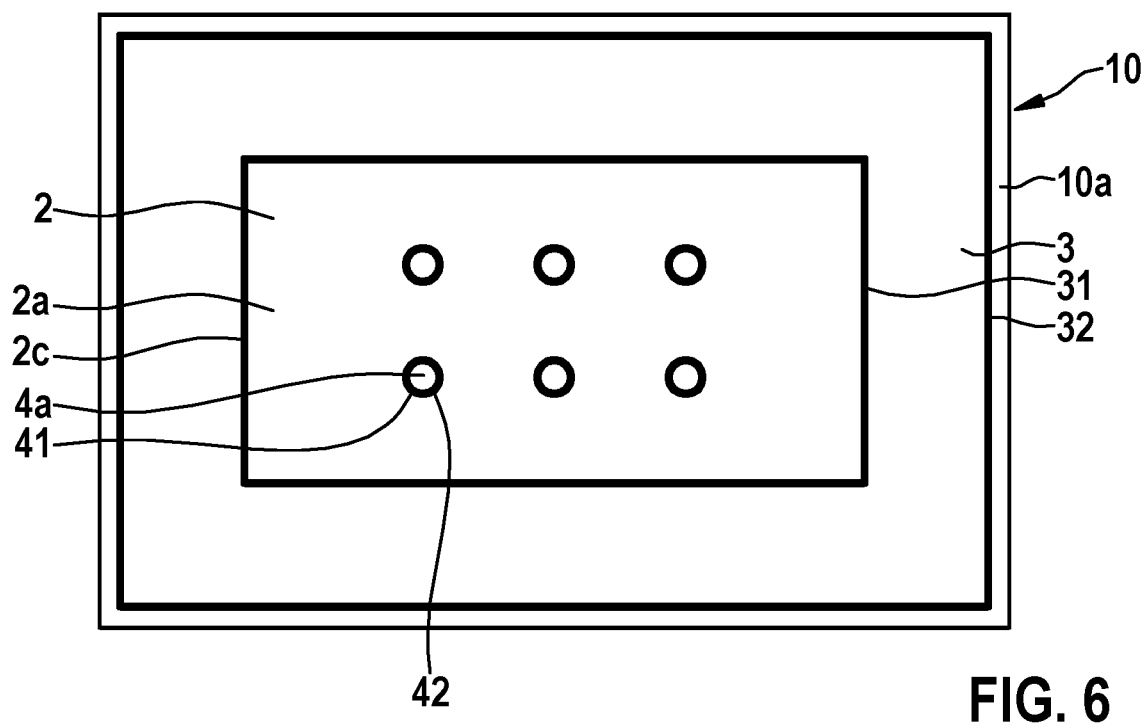
FIG. 6 is a schematical plan view onto the wafer portion of FIGS. 4 and 5 after filling of the blind holes and the recess with a metallic material to form conductors and a flange.
Figure 7:
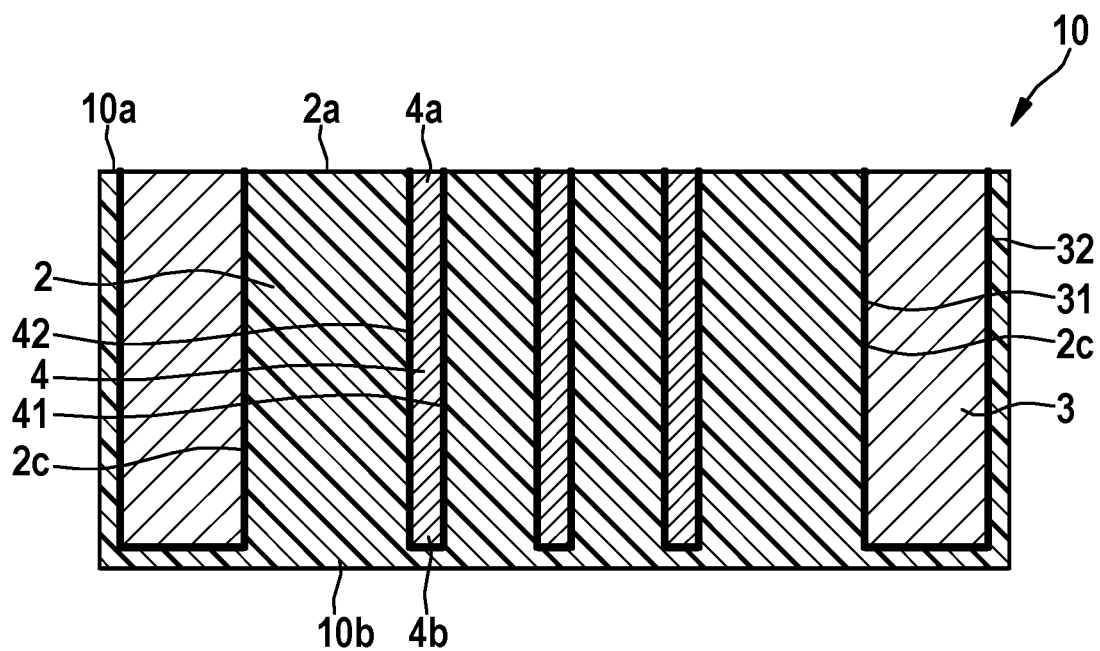
FIG. 7 is a schematical cross section view of the wafer portion shown in FIG. 6.

After forming of the blind holes 40/recess 30, a metallic material is arranged in the blind holes 40 of the respective wafer portion 10 to form conductors 4, so that each conductor 4 comprises a first end 4*a* at the front side 10*a* of the respective wafer portion 10 and a second end 4*b* at a bottom of the respective blind hole 40. A further metallic material is filled in the recess 30 of the respective wafer portion 10 to form a flange 3 of the respective wafer portion 10. This is indicated in FIGS. 6 and 7. Particularly, the metallic material and the further metallic material can be identical.

Particularly, the blind holes 40 and/or the respective recess 30 in the front side 10*a* of the respective wafer portion 10 can be formed by patterning the front side 10*a* of the respective wafer portion 10 with a photoresist (PR) followed by a dry etching process such as e.g. RIE (reactive ion etching). Alternatively, inductive coupled plasma (ICP) or ion milling can be used. As a further alternative, the blind holes 40 and/or the recess 30 of the respective wafer portion 10 can also be formed using a laser.

To improve adhesion of the metallic material filled into the blind hole or of the further metallic material filled into the recess of the respective wafer portion 10, a coating 42 can be applied to an inner side 41 of the respective blind hole 40 of the respective wafer portion 10 before the metallic material is filled in the blind holes 40 of the respective wafer portion. Correspondingly, such a coating 32 can be applied to an inner side 31 of the recess 30 of the respective wafer portion 10 before the further metallic material is filled in the recess 30 of the respective wafer portion 10. Particularly, the coating 42, 32 of the inner sides 41, 31 of the blind holes 40 or of the recesses 30 can be a metallization process. Such a metallization 42, 32 can comprise one or a combination of Ti, Ta, an alloy comprising Ti and W, Ni (e.g. in form of a Ni seed layer). The respective coating 42, 32 can be applied by way of suitable methods such as physical vapor deposition (PVD), sputtering, or evaporation. The thickness of the respective coating/metallization 42, 32 can be in the range from e.g. 0.1 µm to 1 µm.

Furthermore, the blind holes 40 and/or the recess 30 of the respective wafer portion 10 can be filled (e.g. after applying the coatings 32, 42) with the respective metallic material by a CVD process (depositing of e.g. one of W, Ni, Ti), or by plating (e.g. Ni).

After filling of the blind holes 40/recess 30, the front side 10*a* of the respective wafer portion 10 can be planarized, if necessary, by way of suitable methods (e.g. CMP).

Figure 8:
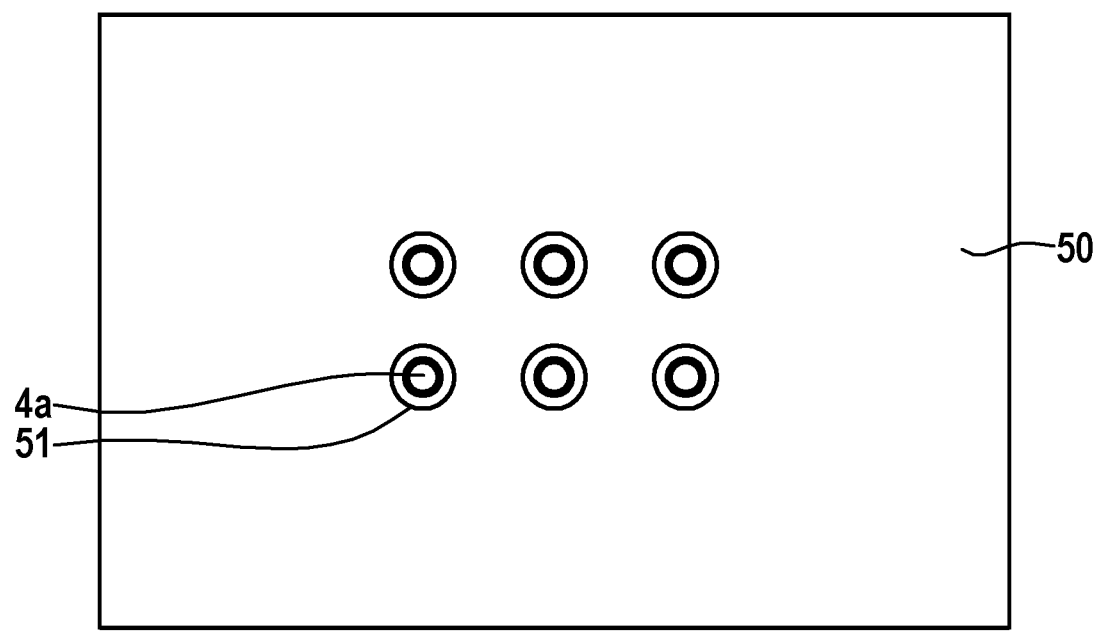
FIG. 8 is a schematical plan view of first contact pads on first ends of the conductors.
Figure 9:
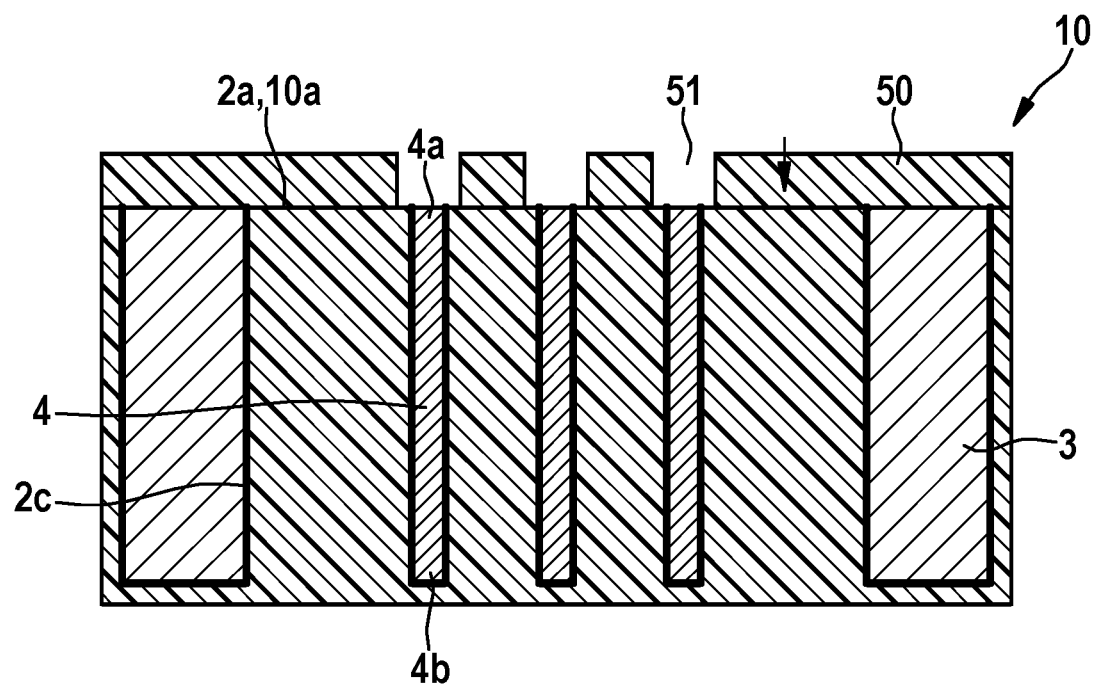
FIGS. 9 to 11 are schematical cross section views showing the forming of the first contact pads on the first ends of the conductors.
Figure 10:
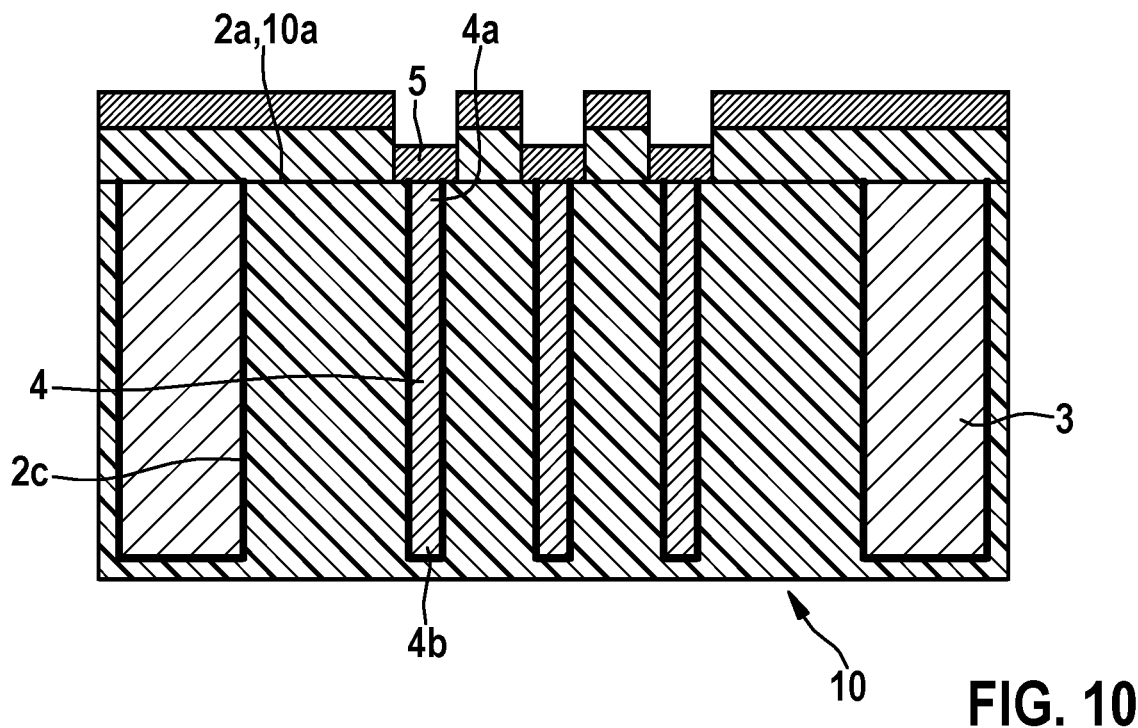
Figure 11:
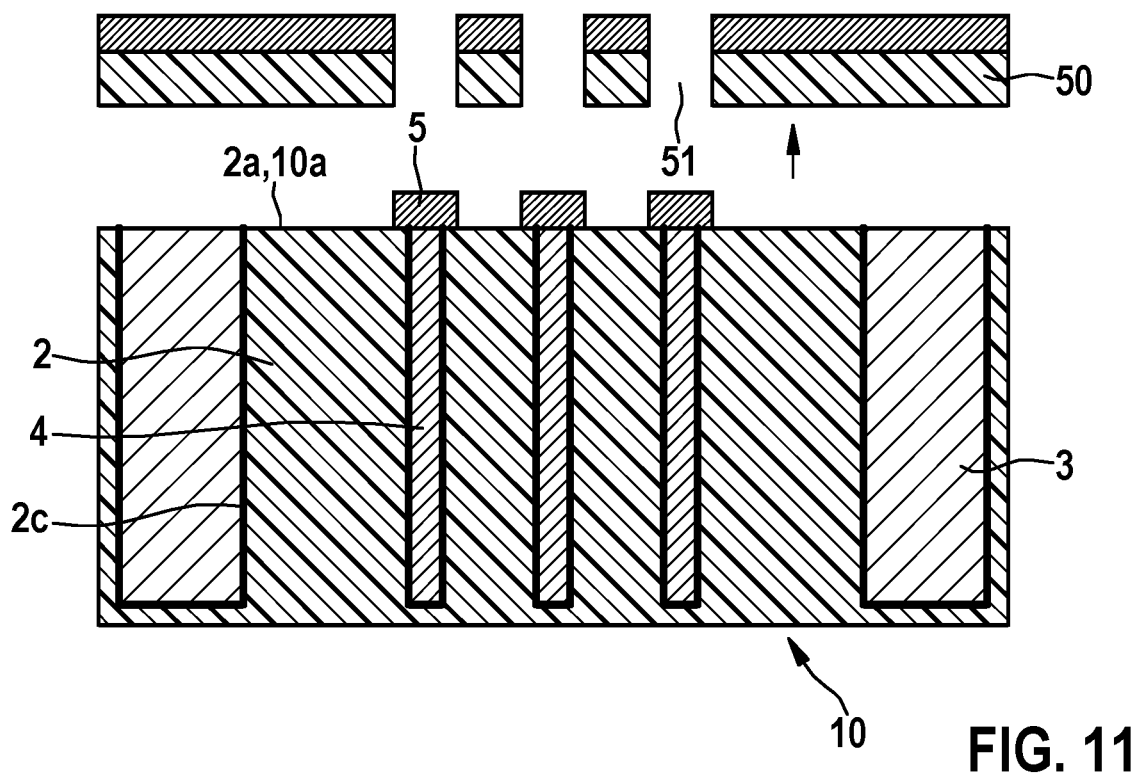
Figure 12:
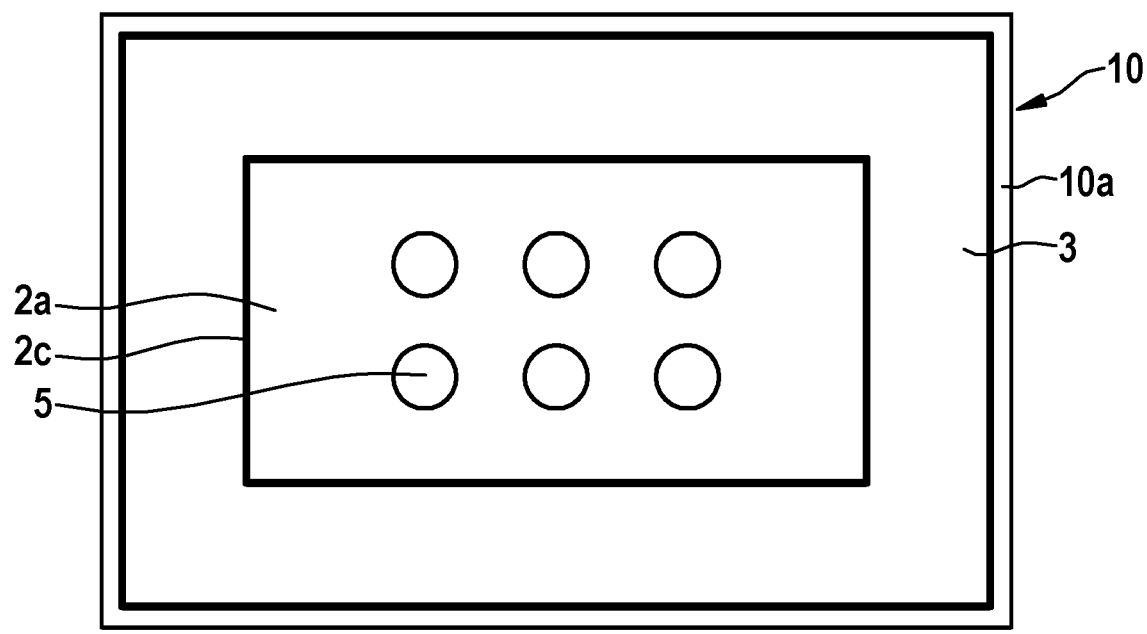
FIG. 12 is a schematical plan view showing the forming of the first contact pads on the first ends of the conductors.

In order to form first contact pads 5 on the front side 10*a* of the respective wafer portion 10, the front side 10*a* of the respective wafer portion can be covered by a mask 50 as shown in FIGS. 8 and 9 such that the first ends 4*a* of the conductors 4 at the front side 10*a* of the respective wafer portion 10 are not covered by the mask 50. Then, as shown in FIG. 10 a further metallic material can be deposited on the non-covered first ends 4*a* of the conductors 4 (through holes 51 of the mask 50) to form the first contact pads 5. Afterwards, as shown in FIG. 11, the mask 50 can be removed from the front side 10*a* of the respective wafer portion 10 which now comprises the first contact pads 5 formed on the conductors 4 as shown in FIGS. 11 and 12. Particularly, the first contact pads 5 can be formed out of a metal such as e.g. one or a combination of Au, Pt, Nb, Ti, that can be evaporated or sputtered onto the first ends 4*a* of the conductors 4 through the holes 51 in the mask 50.

Figure 13A:
FIGS. 13A to 13B are plan views for show the forming of second contact pads on the second ends of the conductors.
Figure 13B:
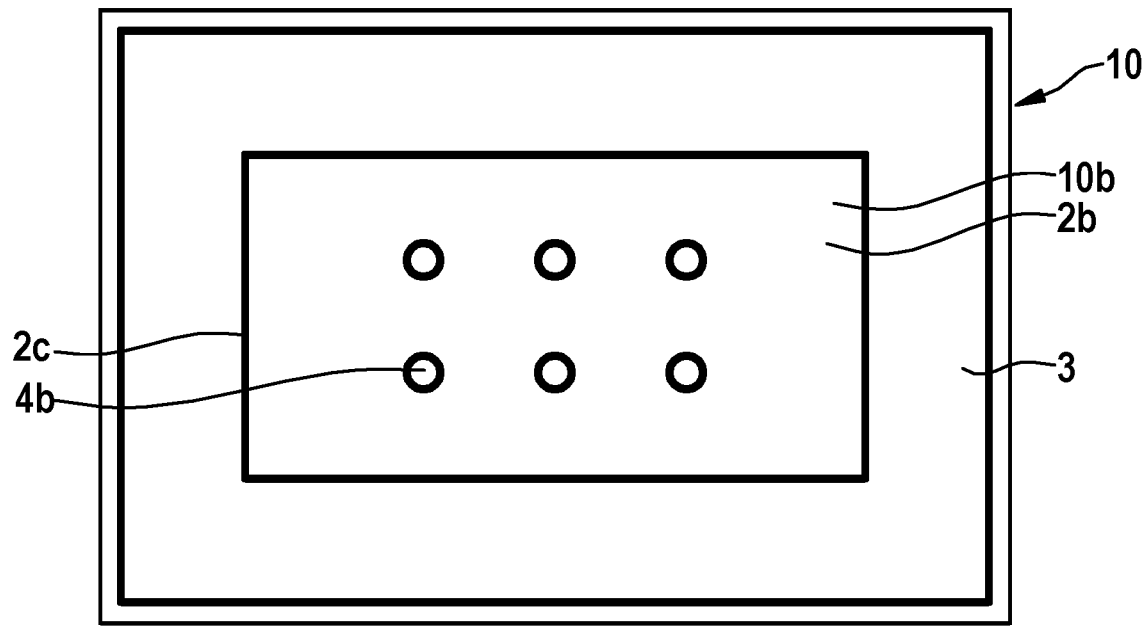
Figure 14A:
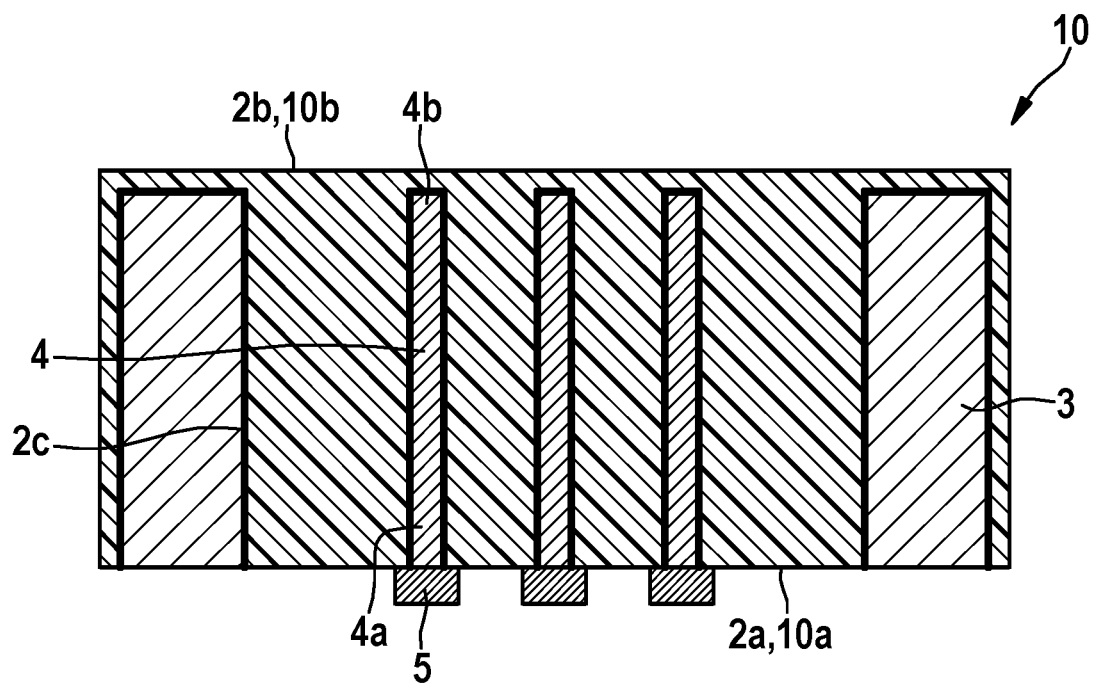
FIGS. 14A to 14B are schematical cross section views showing the forming of second contact pads on the second ends of the conductors.
Figure 14B:
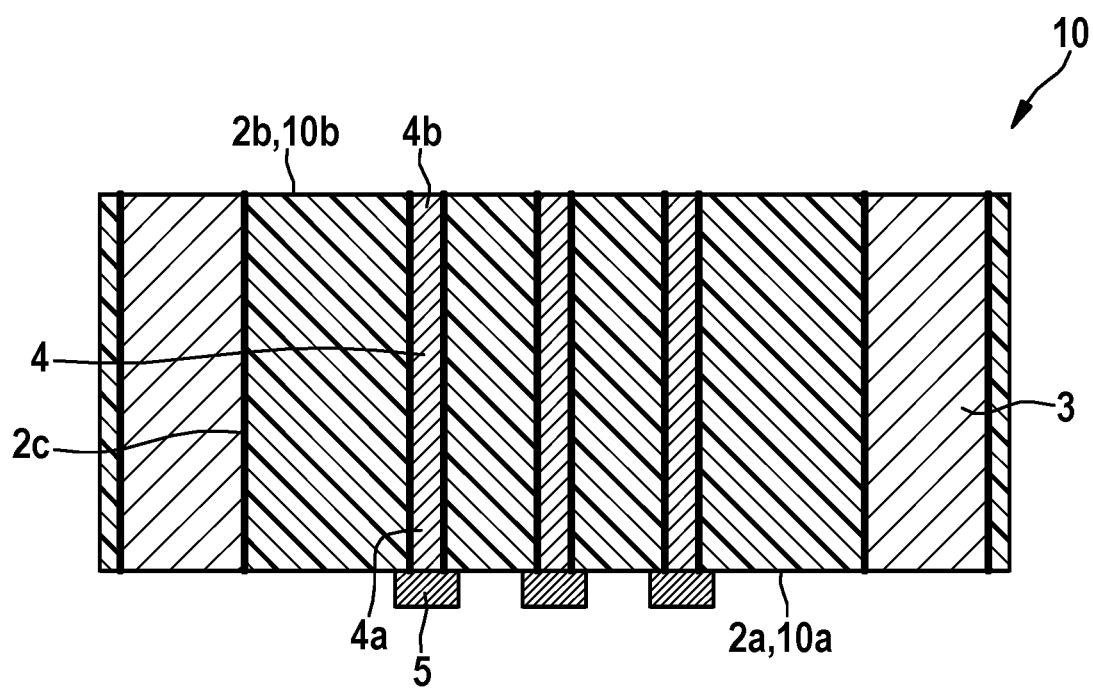

In order to also form second contact pads on the back side 10*b* of the respective wafer portion 10, a first variant of the method can be conducted, wherein a layer on the back side 10*b* of the respective wafer portion 10 is removed by back-grinding or CMP, as shown in FIGS. 13A and 13B as well as FIGS. 14A and 14B so as to expose the second ends 4*b* of the conductors 4 of the respective wafer portion 10.

Figure 26:
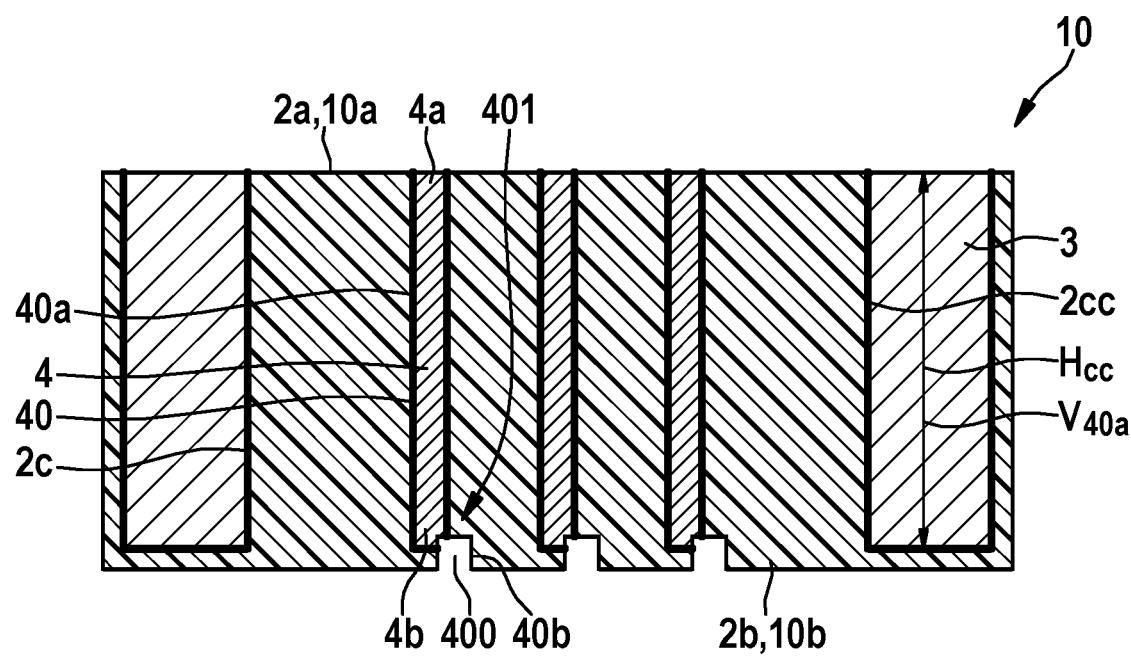
FIGS. 26 to 27 are schematical cross section views showing an alternative way of forming conductors in the respective wafer portion/electrically insulating body of the respective feedthrough connector.
Figure 27:
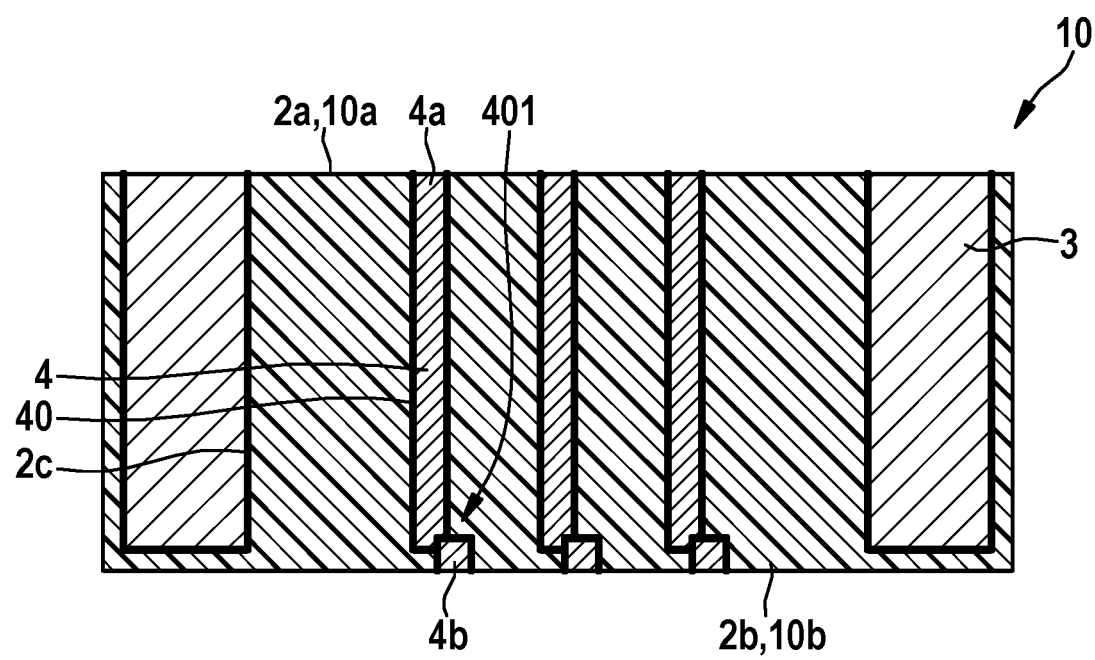

Alternatively, according to a second variant, which is shown in FIGS. 26 and 27, a plurality of holes 400 can be formed in the back side 10*b* of the respective wafer portion 10 instead, wherein each of the holes 400 is arranged offset with respect to an associated blind hole 40 formed in the front side 10*a* of the respective wafer portion (as described above), such that the respective hole 400 exposes a portion of the conductor 4 in the associated blind hole 40. Then, the metallic material used for forming the conductors 4 is deposited in the newly formed holes 400 in the back side 10*b* of the respective wafer portion 10 to form a narrowing 401 of the respective conductor 4 and to prolong the respective conductor 4 such that it extends with its second end 4*b* up to the back side 10*b* of the respective wafer portion 10 as indicated in FIG. 27. Also here, a coating can be applied to an inner side of the respective hole 400 (using e.g. one of the materials stated with respect to the coating 42 of the blind holes 40) before the metallic material is filled into the holes 400.

Figure 15:
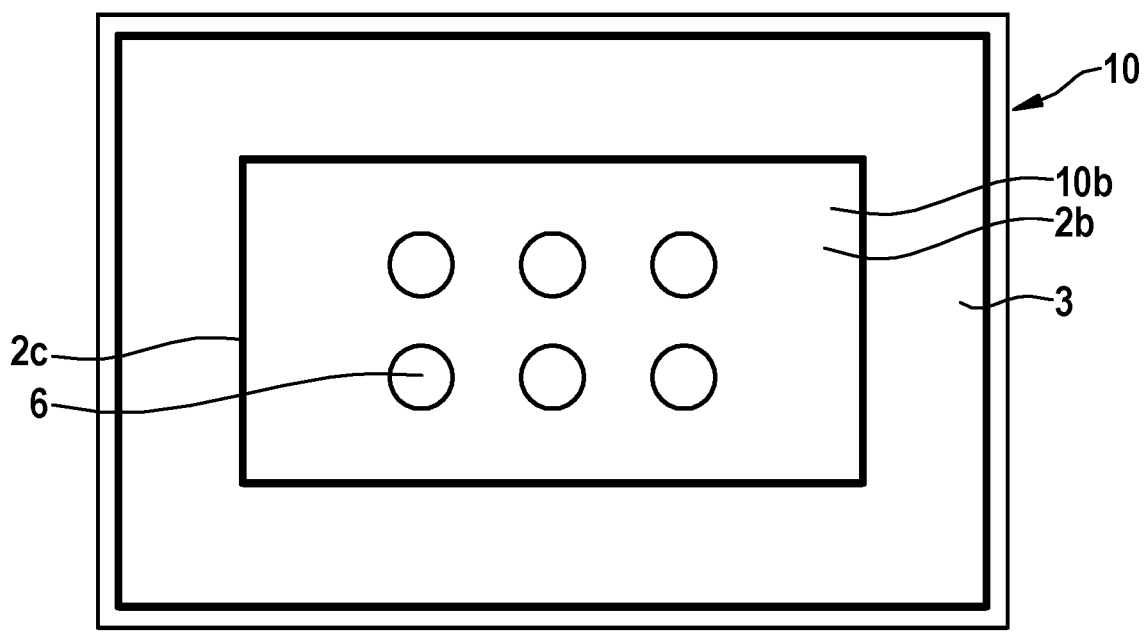
FIG. 15 is a plan view for forming the second contact pads on the second ends of the conductors.
Figure 16:
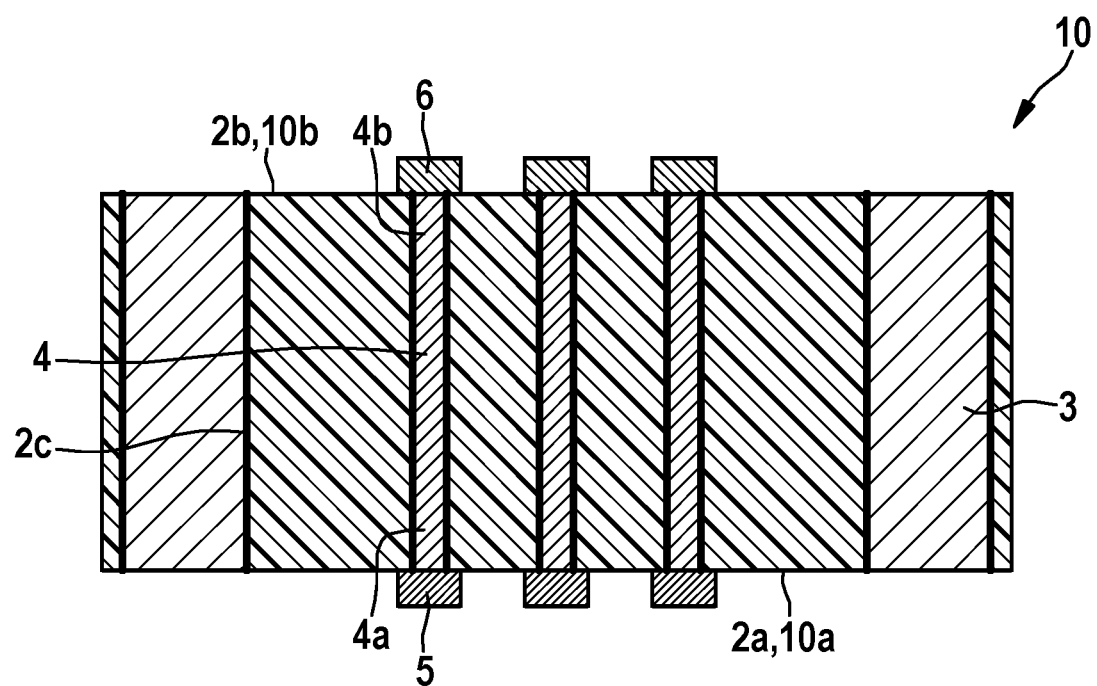
FIG. 16 is a schematical cross section view showing the forming of second contact pads on the second ends of the conductors.

Now, in order to form second contact pads 6 on the second ends 4*b* of the conductors 4 as shown in FIGS. 15 to 16 again a mask can be used as in case of the first contact pads 5. Also here, a mask is arranged on the back side 10*b* of the respective wafer portion 10 such that the second end 4*b* of the respective conductor at the back side 10*b* of the respective wafer portion 10 is not covered by the mask (not shown). Then, a further metallic material is deposited on the non-covered second end 4*b* of the respective conductor 4 to form a second contact pad 6 thereon. After forming of the second contact pads 6 the mask is removed from the back side 10*b* of the respective wafer portion 10. The further metallic material for the second contact pads 6 can comprise or can be formed by the materials stated above with respect to the second contact pads 6. Particularly, this further metallic material can comprise or can be one of the following (e.g. solderable) metals: Sn/Ni, Cu/Ni, Sn/Pb, Pt, Rh, Nb, an alloy comprising Sn, Ag, and Cu.

Figure 17:
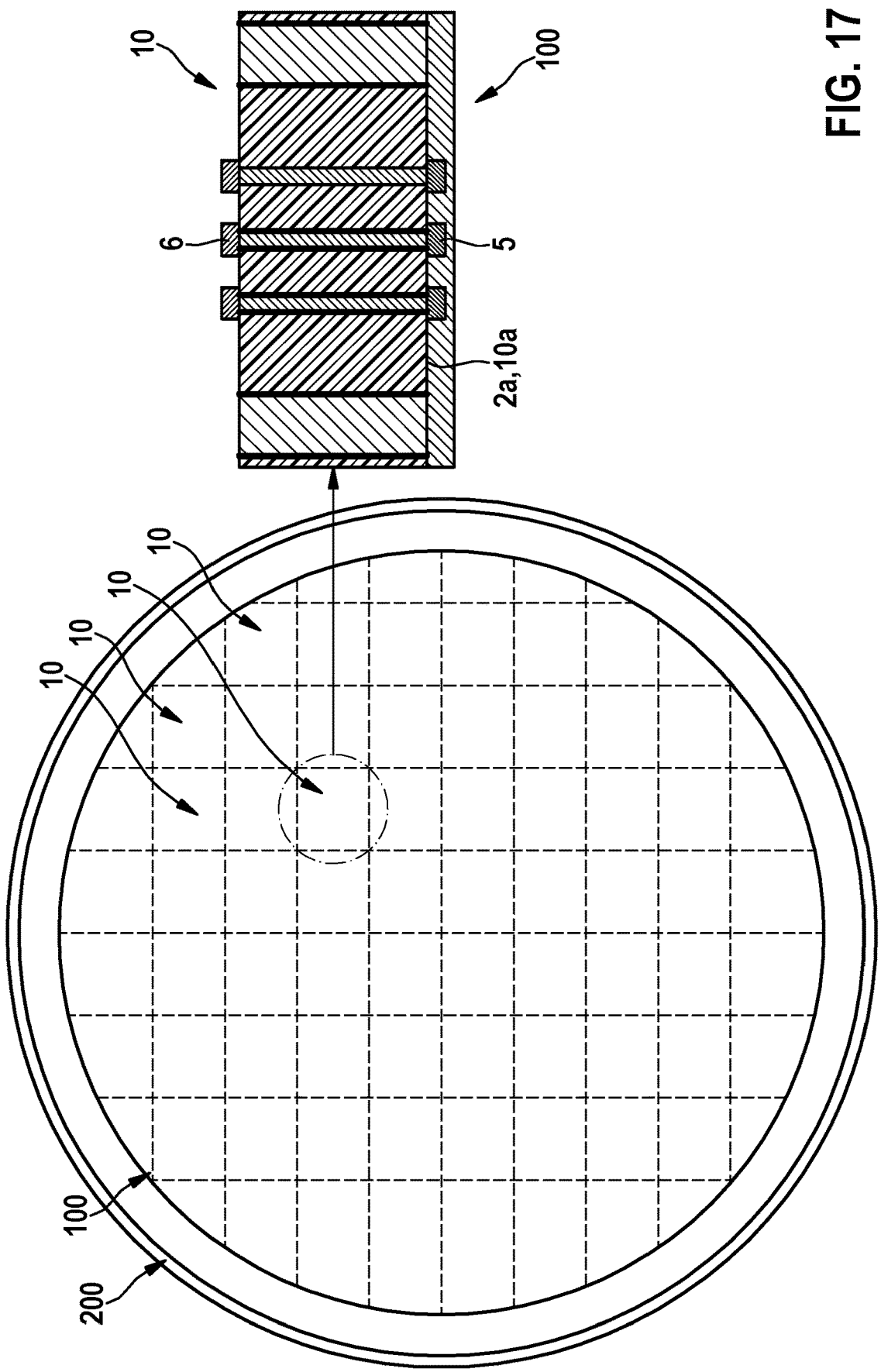
FIG. 17 is an illustration showing a mounting of the glass wafer onto a carrier.

In order to separate the individual wafer portions 10 from one another and exposing the flange so as to produce the final feedthrough connectors 1 each comprising an electrically insulating body 2 formed from the respective wafer portion 10, the glass wafer 100 (i.e. the connected wafer portion 10) is mounted on a carrier 200 as shown in FIG. 17, wherein particularly the front side 10*a* of the respective wafer portion 10 is arranged on the carrier 200.

Particularly, exposing the flange and separation of the wafer portions 10 from one another can be conducted as shown in FIGS. 18 to 21 by removing a region 10*c* of each wafer portion 10 that surrounds the flange 3 of the respective waver portion 10 so that a circumferential lateral side 3*c* of the flange 3 of the respective wafer portion 10 is exposed and the remaining portion 2 of the respective wafer portion 10 forms the electrically insulating body 2 of the respective feed through connector 1 resting on the carrier 200.

Figure 18:
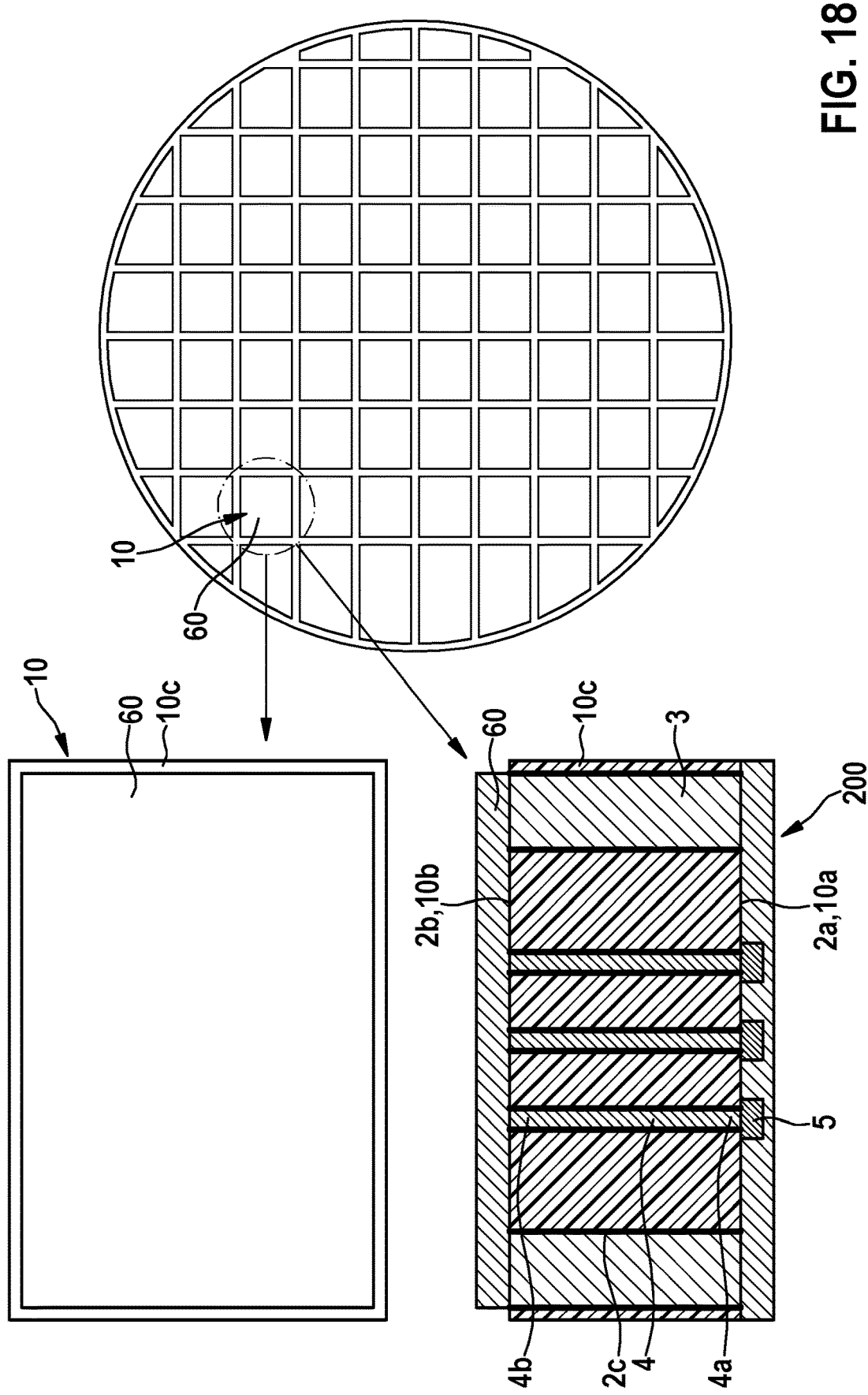
FIGS. 18 to 21 are illustrations for showing the step of releasing the flanges and thereby separating of the individual feedthrough connectors.
Figure 19:
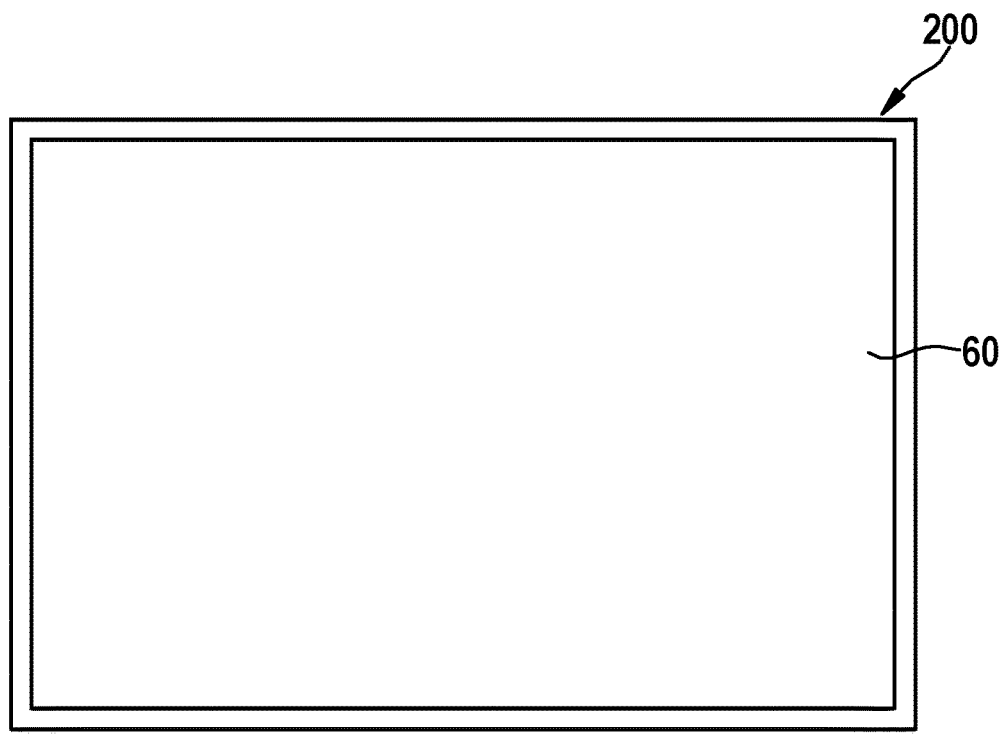
Figure 20:
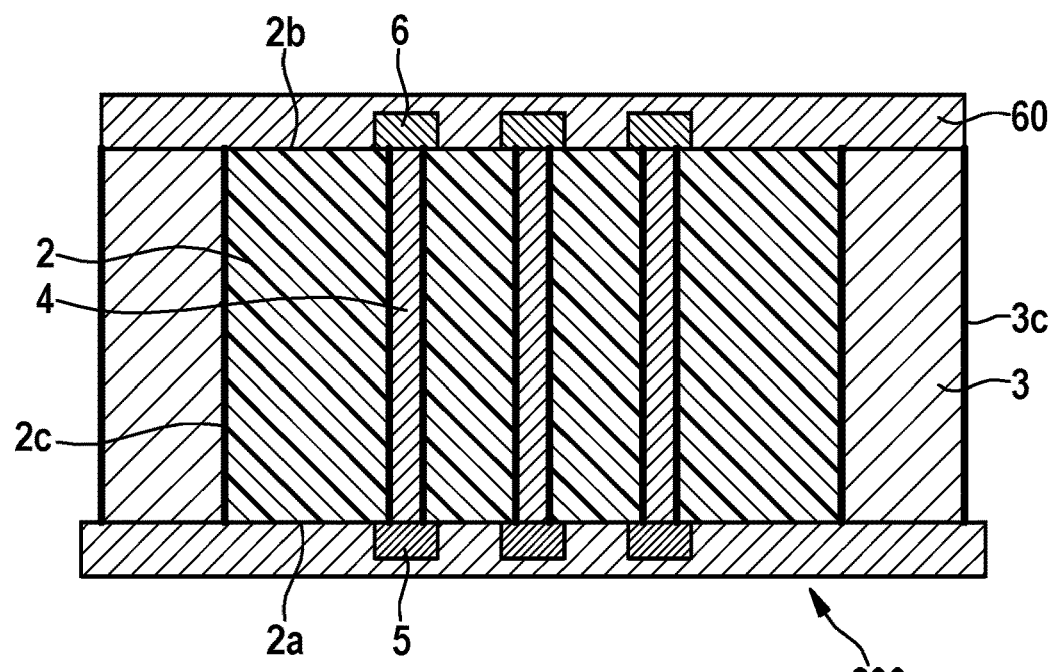
Figure 21:
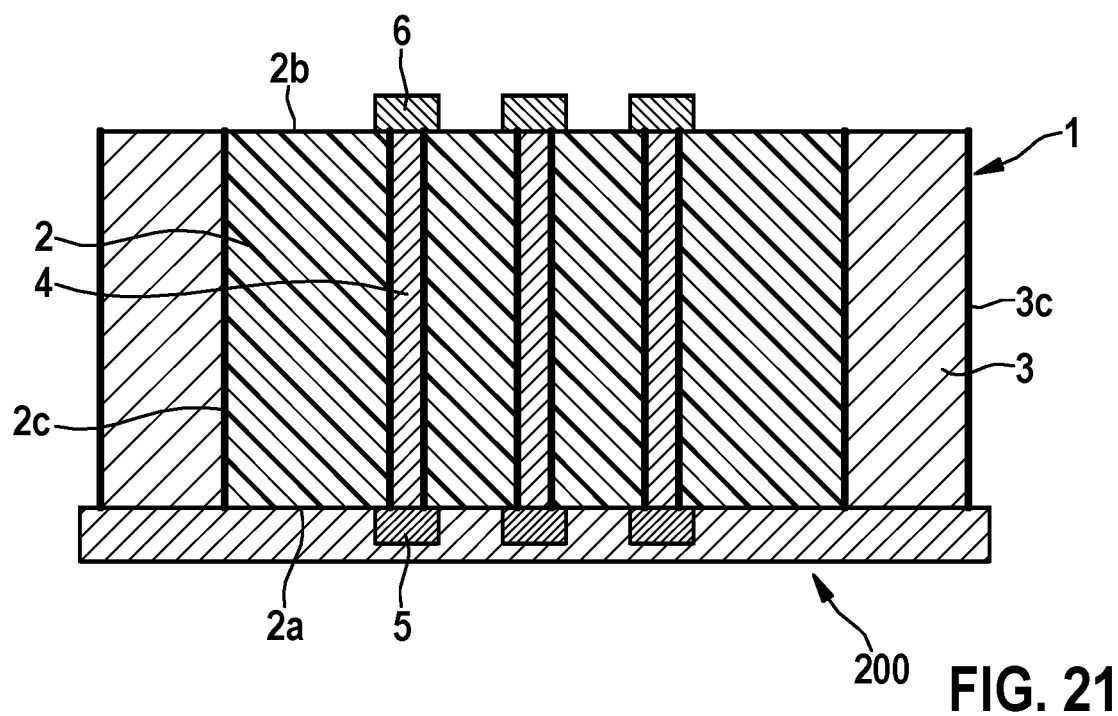

Particularly, as shown in FIG. 18, for separating the wafer portions 10 from one another, a mask 60 can be arranged on the back side 10*b* of each carrier portion 10, which mask 60 extend on the back side 10*b* of the respective wafer portion 10 up to an outer edge of the flange 3 of the respective wafer portion 10 so that the region 10*c* of the respective wafer portion 10 is not covered by the mask 60. Particularly, the mask's protective metal can be formed by Ni or Al metal layers highly selective to dry etch chemistry. Alternatively, conventional lithography can be used to deposit a mask such as SU8 on the back side 10b of the respective wafer portion 10.

After positioning of the mask 60, the region 10c of the respective wafer portion 10 is removed by way of etching using e.g. a RIE dry etching process. Alternatively, the region 10c of the respective wafer portion 10 can be removed by means of a laser to separate the wafer portions 10/feedthrough connectors 1 from one another. Particularly, such a laser based singulation can be followed by a wet or dry chemical process to remove residual glass and expose the flange 3 of the respective wafer portion 10/feedthrough connector 1.

Figure 22:
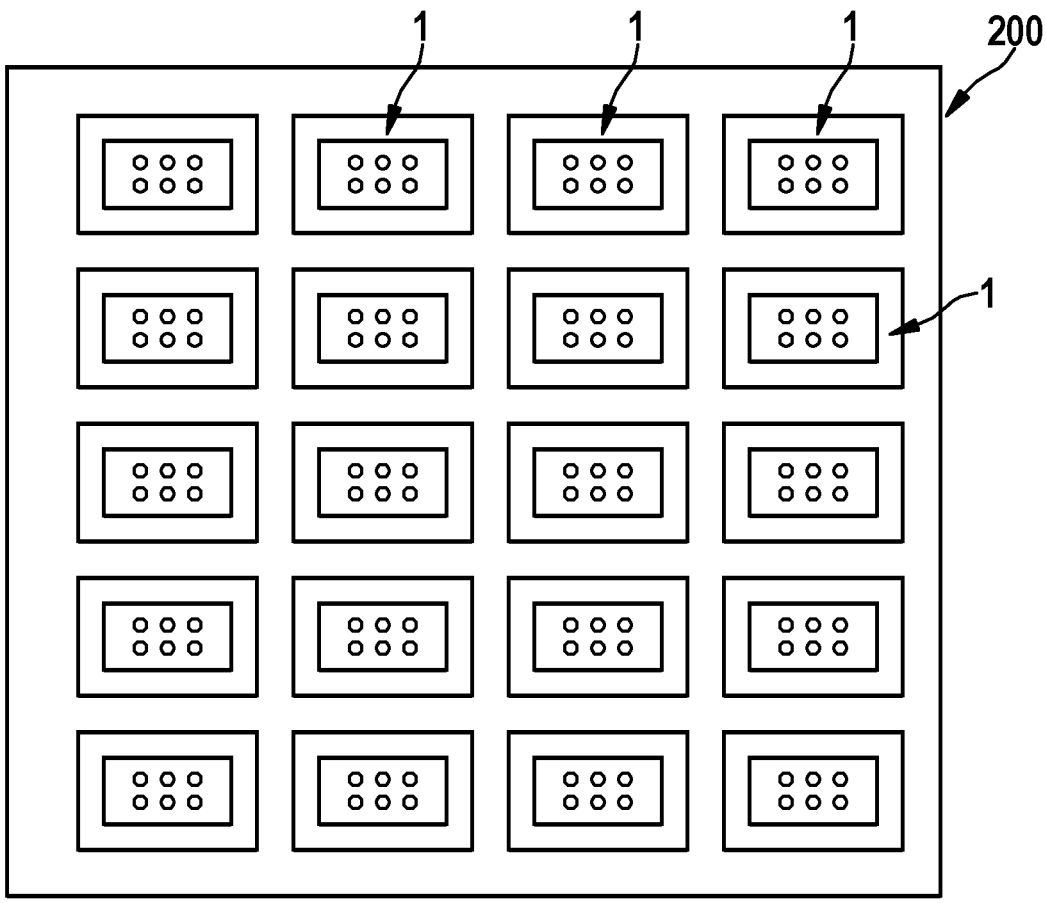
FIGS. 22 to 23 are illustrations showing the carrier with the separated feedthrough connectors arranged thereon.
Figure 23:
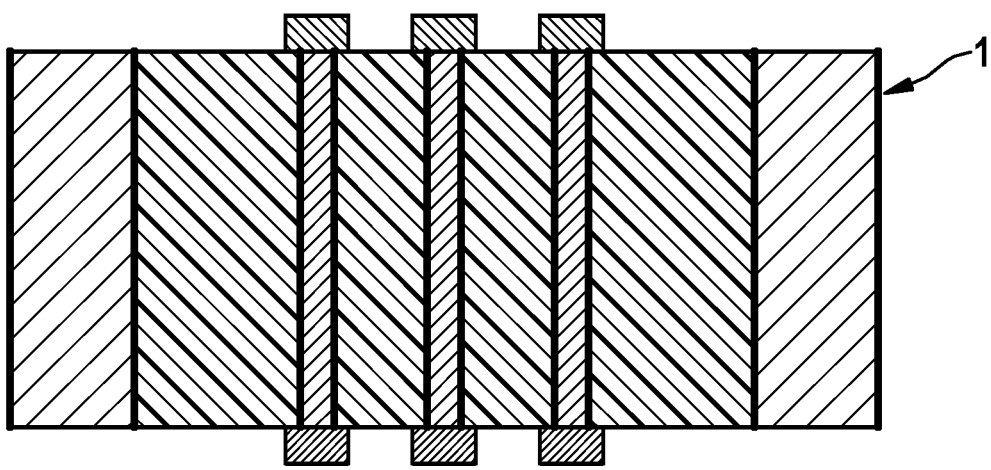

After separating the individual wafer portions 10, a corresponding plurality of feedthrough connectors 1 rest on the carrier 200 as indicated in FIGS. 22 and 23. The individual feedthrough connector 1 can now be mounted to a device such as an implantable medical device 11 as shown in FIGS. 24 and 25.

Figure 24:
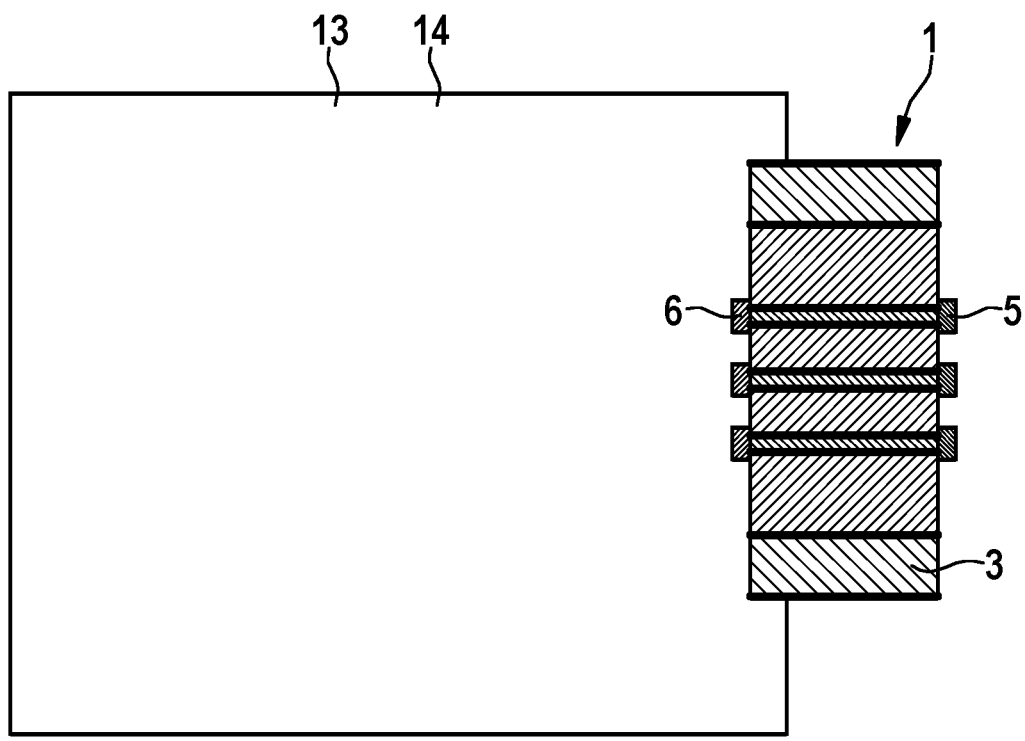
FIGS. 24 to 25 are illustrations showing the connecting of a feedthrough connector to an electrical circuit and a housing of an implantable medical device.
Figure 25:
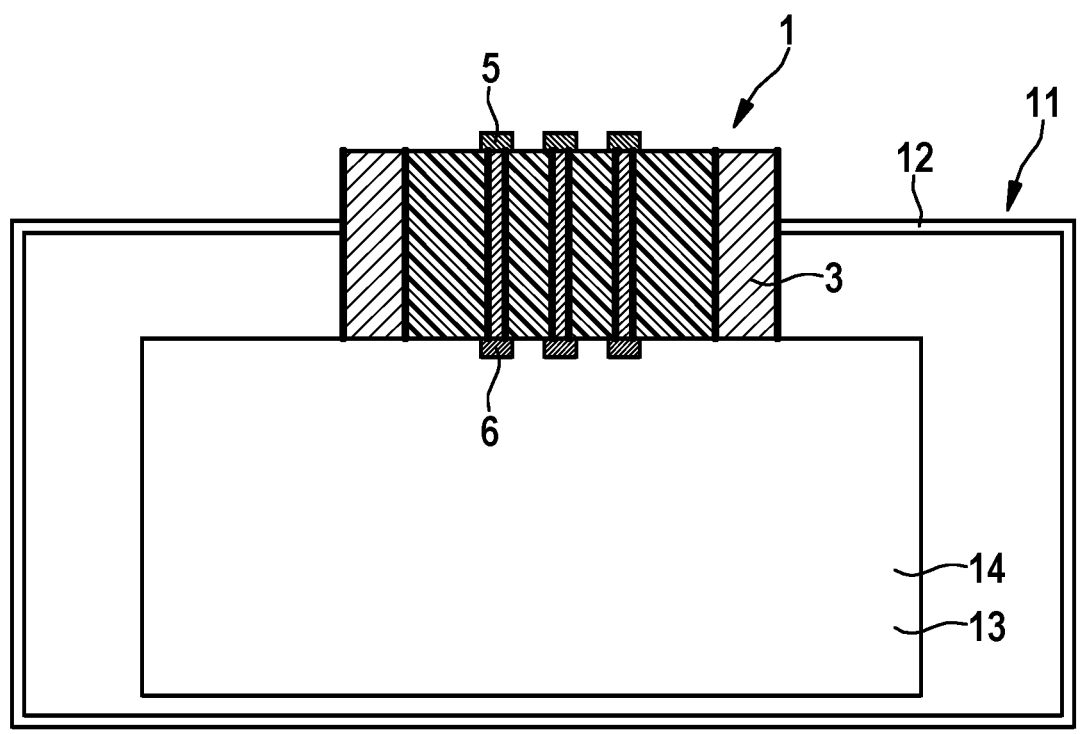

Particularly, according to FIG. 24, the second contact pads 6 are connected, particularly welded or soldered, to corresponding contacts of an electrical circuit 13 of the medical device 11 which circuit can be arranged on a substrate 14 (e.g. printed circuit board).

Furthermore, the flange 3 of the feedthrough connector 1 is welded in a hermetically sealed fashion to a housing 12 of the medical device 11. The feedthrough connector now provides a hermetically sealed interface for making electrical connections to the circuit 13 via the first contact pads 5 being arranged outside of the housing. For instance, the implantable medical device 11 can be an implantable cardiac pacemaker and the feedthrough connector 1 can provide electrical connections to a header of the pacemaker 11.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

The invention claimed is:

1. A method for producing a feedthrough connector, which comprises the steps of:
    providing a glass wafer having at least one wafer portion, the at least one wafer portion having a front side and a back side facing away from the front side;
    forming a plurality of blind holes and a circumferential recess in the front side of the at least one wafer portion such that the circumferential recess surrounds the blind holes;
    filling a metallic material into the blind holes of the at least one wafer portion to form conductors, wherein each of the conductors having a first end at the front side of the at least one wafer portion and a second end at a bottom of each of the blind holes; and
    filling a further metallic material into the circumferential recess of the at least one wafer portion to form a flange of the at least one wafer portion.

2. The method according to claim 1, which further comprising:
    applying a coating to an inner side of a respective blind hole of the at least one wafer portion before the metallic material is filled into the blind holes of the at least one wafer portion; and/or
    applying a coating to an inner side of the circumferential recess of the at least one wafer portion before the further metallic material is filled into the circumferential recess of the at least one wafer portion.

3. The method according to claim 1, which further comprises:
    masking the front side of the at least one wafer portion with a mask such that the first end of the conductors at the front side of the at least one wafer portion are not covered by the mask;
    depositing a further metallic material on non-covered first ends of the conductors to form first contact pads; and
    removing the mask from the front side of the at least one wafer portion after forming the first contact pads.

4. The method according to claim 1, which further comprises removing a layer on the back side of the at least one wafer portion so as to expose the second end of the conductors of the at least one wafer portion.

5. The method according to claim 1, which further comprises forming a plurality of holes in the back side of the at least one wafer portion, wherein each of said holes is disposed offset with respect to an associated one of the blind holes formed in the front side of the at least one wafer portion, such that a respective hole exposes a portion of a conductor in an associated blind hole, and filling the metallic material into the holes in the back side of the at least one wafer portion to form a narrowing of a respective conductor and to prolong the respective conductor such that it extends with the second end towards the back side of the at least one wafer portion.

6. The method according to claim 4, which further comprises:
    masking the back side of the at least one wafer portion with a mask such that the second end of a respective conductor at the back side of the at least one wafer portion is not covered by the mask, and wherein a further metallic material is deposited on a non-covered second end of the respective conductor to form a second contact pad connected to the respective conductor; and
    removing the mask from the back side of the at least one wafer portion after forming second contact pads.

7. The method according to claim 1, which further comprises mounting the glass wafer on a carrier.

8. The method according to claim 1, which further comprises removing a region of the at least one wafer portion that surrounds the flange of the at least one wafer portion so that a circumferential lateral side of the flange of the at least one wafer portion is exposed and a remaining portion of the at least one wafer portion forms an electrically insulating body of the feed through connector resting on the carrier.

9. The method according to claim 1, wherein the at least one wafer portion is one of a plurality of wafer portions connected to each other.

10. The method according to claim 7, wherein the front side of the at least one wafer portion is disposed on the carrier.

11. A feedthrough connector, comprising:
    an electrically insulating body formed out of glass, said electrically insulating body having a front side and a back side facing away from said front side, said electrically insulating body further having a circumferential lateral side extending from said front side to said back side of said electrically insulating body, and said electrically insulating body having a plurality of through-openings formed therein, each of said through-openings extending from said front side to said back side of said electrically insulating body, each of said through-openings defined by a respective first hole segment from front side into said body and a respective second hole segment from backside into said body axially, said respective first hole segment being offset from said respective second hole segment for defining a narrowing of said through-openings;

first contact pads;

second contact pads;

a plurality of electrical conductors, each of said electrical conductors disposed in one of said through-openings such that each of said through-openings is hermetically sealed, wherein a respective conductor of said electrical conductors having a metallic material, said respective conductor having a first end disposed at said front side and connected to one of said first contact pads disposed on said front side, and an opposing second end disposed at said back side and connected to one of said second contact pads disposed on said back side; and a circumferential flange having a further metallic material, wherein said circumferential flange is connected to said circumferential lateral side of said electrically insulating body such that said circumferential flange surrounds said electrically insulating body and contacts said circumferential lateral side of said electrically insulating body.

* * * * *